US011608357B2

(12) United States Patent
Jezek et al.

(10) Patent No.: US 11,608,357 B2
(45) Date of Patent: *Mar. 21, 2023

(54) STABILIZED ANTIBODY PROTEIN SOLUTIONS

(71) Applicant: Arecor Limited, Saffron Walden (GB)

(72) Inventors: Jan Jezek, Saffron Walden (GB); Luca Badiali, Saffron Walden (GB); David Gerring, Saffron Walden (GB)

(73) Assignee: ARECOR LIMITED, Saffron Walden (GB)

( * ) Notice: Subject to any disclaimer, the term of this patent is extended or adjusted under 35 U.S.C. 154(b) by 0 days.

This patent is subject to a terminal disclaimer.

(21) Appl. No.: 16/552,675

(22) Filed: Aug. 27, 2019

(65) Prior Publication Data
US 2020/0071352 A1 Mar. 5, 2020

Related U.S. Application Data

(60) Provisional application No. 62/723,549, filed on Aug. 28, 2018.

(51) Int. Cl.
*A61K 39/395* (2006.01)
*C07K 1/02* (2006.01)
*C07K 16/22* (2006.01)
*C07K 16/06* (2006.01)

(52) U.S. Cl.
CPC .............. *C07K 1/02* (2013.01); *C07K 16/065* (2013.01); *C07K 16/22* (2013.01); *C07K 2317/94* (2013.01)

(58) Field of Classification Search
None
See application file for complete search history.

(56) References Cited

U.S. PATENT DOCUMENTS

| 8,241,632 B2 | 8/2012 | Rehder et al. |
| 9,382,317 B2 | 7/2016 | Manning et al. |
| 2003/0138417 A1 | 7/2003 | Kaisheva et al. |
| 2004/0033228 A1 | 2/2004 | Krause et al. |
| 2008/0112953 A1 | 5/2008 | McAuley et al. |
| 2012/0301460 A1 | 11/2012 | Bao et al. |
| 2013/0209465 A1 | 8/2013 | Jezek et al. |
| 2014/0141008 A1 | 5/2014 | Fraunhofer et al. |
| 2020/0016074 A1 | 1/2020 | Badiali et al. |
| 2020/0016075 A1 | 1/2020 | Badiali et al. |
| 2020/0023061 A1 | 1/2020 | Jezek et al. |
| 2020/0023062 A1* | 1/2020 | Jezek ..................... A61K 47/10 |
| 2020/0069799 A1 | 3/2020 | Jezek et al. |

FOREIGN PATENT DOCUMENTS

| EP | 2238985 A1 | 10/2010 |
| EP | 3372241 A1 | 9/2018 |
| EP | 3372242 A1 | 9/2018 |
| WO | WO97/29131 A1 | 8/1997 |
| WO | WO01/87329 A1 | 11/2001 |
| WO | WO03/072060 A2 | 9/2003 |
| WO | WO 2004/007520 A1 | 1/2004 |
| WO | WO2006/081587 A2 | 8/2006 |
| WO | WO2006/096488 A2 | 9/2006 |
| WO | WO2007/109221 A2 | 9/2007 |
| WO | WO2008/084237 A2 | 7/2008 |
| WO | WO 2008/157356 A1 | 12/2008 |
| WO | WO2010/062896 A1 | 6/2010 |
| WO | WO2012/013980 A1 | 2/2012 |
| WO | WO2013/011076 A2 | 1/2013 |
| WO | WO2013/114112 A2 | 8/2013 |
| WO | WO2013/164837 A1 | 11/2013 |
| WO | WO2014/039903 A2 | 3/2014 |
| WO | WO2014/114651 A9 | 7/2014 |
| WO | WO2016/066688 A1 | 5/2016 |
| WO | WO2016/103093 A1 | 6/2016 |
| WO | WO 2016/109822 A1 | 7/2016 |
| WO | WO2016/120413 A1 | 8/2016 |
| WO | WO2016/162819 A1 | 10/2016 |
| WO | WO2018/011404 A1 | 1/2018 |
| WO | WO2018/154319 A1 | 8/2018 |
| WO | WO2018/154320 A1 | 8/2018 |
| WO | WO2018/162500 A1 | 9/2018 |
| WO | WO2018/162503 A1 | 9/2018 |
| WO | WO2018/184692 A1 | 10/2018 |
| WO | WO2018/184693 A1 | 10/2018 |

OTHER PUBLICATIONS

Akers, M. J., et al., "Formulation Development of Protein Dosage Forms," Development and Manufacture of Protein Pharmaceuticals. Pharmaceutical Biotechnology, 14:47-127 (2002).
Carpenter, J. F., "Rational Design of Stable Lyophilized Protein Formulations: Some Practical Advice," Pharmaceutical Research, 14(8):969-975 (1997).
Vagenende, V., et al., "Mechanisms of Protein Stabilization and Prevention of Protein Aggregation by Glycerol," Biochemistry, 48:11084-11096 (2009).
Wang, W., "Instability, stabilization, and formulation of liquid protein pharmaceuticals," Int'l Journal of Pharmaceutics, 185:129-188 (1999).
Manning et al., "Stability of Protein Pharmaceuticals: An Update", Pharmaceutical Research, vol. 27, No. 4, Apr. 2010.
Nicoud et al., "Effect of polyol sugars on the stabilization of monoclonal antibodies", Elsevier Biophysical Chemistry 197:40-46 (2015).
U.S. Appl. No. 16/552,682, filed Aug. 27, 2019, Jezek et al.
U.S. Appl. No. 16/491,500, filed Sep. 5, 2019, Badiali et al.
U.S. Appl. No. 16/491,506, filed Sep. 5, 2019, Badiali et al.
U.S. Appl. No. 16/487,990, filed Aug. 22, 2019, Jezek et al.
U.S. Appl. No. 16/487,999, filed Aug. 22, 2019, Jezek et al.

\* cited by examiner

*Primary Examiner* — Yunsoo Kim

(74) *Attorney, Agent, or Firm* — Nixon & Vanderhye P.C.

(57) ABSTRACT

There is provided, inter alia, an aqueous solution comprising (i) an antibody protein; and (ii) a antibody protein stabilizing mixture of arginine, methionine, and a C3 polyol.

47 Claims, No Drawings

STABILIZED ANTIBODY PROTEIN SOLUTIONS

CROSS-REFERENCE TO RELATED APPLICATIONS

This application claims the benefit of U.S. Provisional Patent Application No. 62/723,549, filed Aug. 28, 2018, which is incorporated herein by reference in its entirety.

BACKGROUND

When formulated as aqueous solutions, antibody proteins are susceptible to structural degradation during storage The processes involved in protein degradation can be divided into physical (e.g. loss of quaternary, tertiary or secondary structure, aggregation, particle formation) and chemical (i.e. processes involving a covalent change such as deamidation, aspartate isomerization, oxidation, hydrolytic clipping etc.). Each of the degradants (e.g. soluble aggregated species, insoluble aggregated species and chemically modified variants) can impact the biological activity, toxicity or immunogenicity of the antibody protein.

Therefore, the level of all degradants has to be kept within the tight specifications that are set for each antibody protein product. The rates of the degradation processes depend on temperature and antibody proteins are generally more stable at lower temperatures. Consequently, commercial antibody products must typically be stored refrigerated. However, with increasing trend toward subcutaneous products that can be self-administered by the patient, there is a strong need to develop antibody protein products that can be used outside the cold chain, at least for a period of time, such as 2 weeks, such as 4 weeks, such as 12 weeks or more. The ability to store the product outside the cold chain often results in considerable improvement in convenience for the patient during the in-use period. Allowed excursions outside the cold chain can also significantly improve shipment logistics.

The present invention addresses the problem of instability of antibody proteins, in particular the problem of antibody protein degradation.

WO2006/081587A2 (Wyeth) describes formulations for maintaining the stability of polypeptides, in particular therapeutic antigen-binding polypeptides such as antibodies. The formulations generally include an antioxidant in a sufficient amount as to inhibit by-product formation, for example, the formation of high molecular weight polypeptide aggregates, low molecular weight polypeptide degradation fragments, and mixtures thereof. The formulations described optionally comprise a tonicity agent, such as mannitol, and a buffering agent or amino acid such as histidine.

WO2007/109221A2 (Wyeth) describes methods of reducing aggregation of a protein in a formulation, comprising adding methionine to the formulation to a concentration of about 0.5 mM to about 145 mM, wherein the method results in reduced aggregation of the protein in the formulation compared with the protein in a formulation lacking methionine.

EP2238985A1 (Chugai Seiyaku) sets out to provide an antibody-containing formulation which is stable and suited for subcutaneous administration, wherein dimerization is prevented during long-term storage. An antibody-containing liquid formulation containing arginine and methionine is described.

WO03/072060A2 (Immunex Corporation) describes a stable aqueous pharmaceutical formulation comprising a therapeutically effective amount of an Fc domain containing polypeptide, and an aggregation inhibitor selected from the group consisting of L-arginine and L-cysteine.

SUMMARY

The present invention addresses the problem of instability of antibody proteins. In one embodiment, the invention relates to an aqueous solution comprising (i) an antibody protein; and (ii) a stabilizing mixture of arginine, methionine and a C3 polyol. In one embodiment, the invention provides a method of stabilizing an antibody protein in an aqueous solution (e.g. for storage) comprising the step of adding to the solution a stabilizing mixture of arginine, methionine and a C3 polyol.

DETAILED DESCRIPTION

The present invention relates to the discovery that an aqueous solution of antibody protein can be stabilized by including a mixture of arginine, methionine and a C3 polyol.

The term "and/or" as used herein, includes the meaning of "and", "or" and all or any other combination of the elements connected by the term.

The term "about" as used herein, means within +/−20%, preferably within +/−15%, more preferably within +/−10%, and most preferably within +/−5% of a given value or range.

The term "substantially" refers to the qualitative condition of exhibiting total or near-total extent or degree of a characteristic or property of interest. One of ordinary skill in the art will understand that biological and chemical phenomena rarely, if ever, achieve or avoid an absolute result. The term "substantially free" means that a referenced component is absent or present at a concentration below detection measured by a selected art-accepted means, or otherwise is present at a level that those skilled in the art would consider to be negligible in the relevant context.

The term "aqueous solution", as used herein, refers to a solution in water, preferably distilled water, deionized water, water for injection, sterile water for injection or bacteriostatic water for injection. The aqueous solutions of the invention include dissolved antibody protein, arginine, methionine and a C3 polyol, and optionally, one or more additives and/or excipients. The aqueous solutions can also include one or more components, such as additives or excipients, which are partially dissolved or undissolved. The presence of such component or components will result in a multi-phase composition, such as a suspension or an emulsion. Preferably, the aqueous solution of the invention is a homogeneous solution, as determined by eye or by light-scattering.

The term "antibody protein", as used herein refers to an antibody, an antibody fragment, an antibody conjugated to an active moiety, a fusion protein comprising one or more antibody fragments, such as an immunoglobulin Fc domain, or a derivative of any of the aforementioned. Examples of derivatives include conjugated derivatives e.g. an antibody or antibody fragment conjugated to another moiety. Such moieties include chemically inert polymers such as PEG. Preferred antibodies include monoclonal antibodies and polyclonal antibodies, preferably monoclonal antibodies. The monoclonal antibodies can be, for example, mammalian (e.g. murine) or avian, chimeric, for example, human/mouse or human/primate chimeras, humanized antibodies or fully human antibodies. Suitable antibodies include an immunoglobulin, such as IgG, including IgG1, IgG2, IgG3 or IgG4, IgM, IgA, such as IgA1 or IgA2, IgD, IgE or IgY. In particular embodiments, the immunoglobulin is IgG1. In other embodiments, the immunoglobulin is IgG2. In other embodiments, the immunoglobulin is IgG3. In other embodiments, the immunoglobulin is IgG4. In other embodiments, the immunoglobulin is IgG2/4.

In some embodiments, the antibody protein contains one or more modifications within an Fc region that alters one or more properties of the antibody protein, such as serum half-life, complement fixation, Fc receptor binding, and/or effector function (e.g. antigen-dependent cellular cytotoxicity).

In some embodiments, the antibody protein contains one or more modifications within an Fc region that alters serum half-life by enhancing antibody binding to FcRn. Such modifications include for example, IgG1-M252Y, S254T, and T256E; IgG1-T250Q and M428L; IgG1-H433K, N434Y; IgG1-N434A; and IgG1-T307A, E380A, N434A (numbering according to Kabat EU index numbering system), and are known in the art (see, e.g. Petkova et al., Int. Immunol. 18:1759-1769 (2006); Dall'Acqua et al., J. Immunol. 169:5171-5180 (2002); Oganesyan et al., Mol. Immunol. 46:1750-1755 (2009); Dall'Acqua et al., J. Biol. Chem. 281:23514-23524 (2006), Hinton et al., J. Immunol. 176: 346-356 (2006); Datta-Mannan et al., Drug Metab. Dispos. 35:86-94 (2007); Datta-Mannan et al., J. Biol. Chem. 282: 1709-1717 (2007); Strohl, Curr. Op. Biotechnol. 20:685-691 (2009); Yeung et al., Immunol. 182:7663-7671 (2009); WO2006/130834; and US Appl. Publ. No. 20170342167, the contents of each of which is herein incorporated by reference in its entirety).

In some embodiments, the antibody protein contains one or more modifications within an Fc region that alters serum half-life by decreasing antibody binding to FcRn. Such modifications include for example, IgG1-M252Y, S254T, T256E; H433K, N434F, 436H; IgG1-I253A; and IgG1-P2571, N434H and D376V, N434H (numbering according to Kabat EU index numbering system), and are known in the art (see, e.g. Petkova et al., Int. Immunol. 18:1759-1769 (2006); Datta-Mannan et al., Drug Metab. Dispos. 35:86-94 (2007); Datta-Mannan et al., J. Biol. Chem. 282:1709-1717 (2007); Strohl, Curr. Op. Biotechnol. 20:685-691 (2009); and Vaccaro et al., Nat. Biotechnol. 23:1283-1288 (2005), and US Appl. Publ. No. 20170342167, the contents of each of which is herein incorporated by reference in its entirety).

In some embodiments, the antibody protein contains one or more modifications within an Fc region that increases antibody dependent cellular cytotoxicity (ADCC). Such modifications include for example, IgG1-S298A, E333A, K334A; IgG1-S239D, I332E; IgG1-S239D, A330L, I332E; IgG1-P2471, A339D or Q; IgG1-D280H, K290S with or without S298D or V; IgG1-F243L, R292P, Y300L; IgG1-F243L, R292P, Y300L, P396L; and IgG1-F243L, R292P, Y300L, V305I, P396L (numbering according to Kabat EU index numbering system), and are known in the art (see, e.g. Bruhns, Blood 113:3716-3725 (2009); Shields, J. Biol. Chem. 276:6591-6604 (2001); Lazar, PNAS 103:4005-4010 (2006); Stavenhagen, Cancer Res. 67:8882-8890 (2007); Horton, Cancer Res. 68:8049-8057 (2008); Zalevsky, Blood 113:3735-3743 (2009); Bruckheimer, Neoplasia 11:509-517 (2009); Strohl, Curr. Op. Biotechnol. 20:685-691 (2009); WO2006/020114; and WO2004/074455, the contents of each of which is herein incorporated by reference in its entirety).

In some embodiments, the antibody protein contains one or more modifications within an Fc region that decreases ADCC. Such modifications include for example, IgG1-K326W, E333S; IgG2-E333S; IgG1-N297A; IgG1-L234A, L235A; IgG2-V234A, G237A; IgG4-L235A, G237A, E318A; IgG4-S228P, L236E; IgG2-118-260; IgG4-261-447; IgG2-H268Q, V309L, A330S, A331 S; IgG1-C220S, C226S, C229S, P238S; IgG1-C226S, C229S, E233P, L234V, L235A; and IgG1-L234F, L235E, P331S (numbering according to Kabat EU index numbering system), and are known in the art (see, e.g. Idusogie et al., J. Immunol. 166:2571-2575 (2001); Sazinsky et al., PNAS 105:20167-20172 (2008); Davis et al., J. Rheumatol. 34:2204-2210 (2007); Bolt et al., Eur. J. Immunol. 23:403-411 (1993); Alegre et al., Transplantation 57:1537-1543 (1994); Xu et al., Cell Immunol. 200:16-26 (2000); Cole et al., Transplantation 68:563-571 (1999); Hutchins et al., PNAS 92:11980-11984 (1995); Reddy et al., J. Immunol. 164:1925-1933 (2000); McEarchern et al., Blood 109:1185-1192 (2007); Strohl, Curr. Op. Biotechnol. 20:685-691 (2009); Kumagai et al., J. Clin. Pharmacol. 47:1489-1497 (2007), WO1997/11971; WO2007/106585; US 2007/0148167A1; the contents of each of which is herein incorporated by reference in its entirety).

In some embodiments, the antibody protein contains one or more modifications within an Fc region that increases complement-dependent cytotoxicity (CDC). Such modifications include for example, IgG1-S298A, E333A, K334A; IgG1-S239D, I332E; IgG1-S239D, A330L, I332E; IgG1-P2471, A339D or Q; IgG1-D280H, K290S with or without S298D or V; IgG1-F243L, R292P, Y300L; IgG1-F243L, R292P, Y300L, P396L; and IgG1-F243L, R292P, Y300L, V305I, P396L (numbering according to Kabat EU index numbering system), and are known in the art (see, e.g. Idusogie et al., J. Immunol. 166:2571-2575 (2001); Strohl, Curr. Op. Biotechnol. 20:685-691 (2009); and Natsume et al., Cancer Res. 68:3863-3872 (2008), the contents of each of which is herein incorporated by reference in its entirety).

In some embodiments, the antibody protein contains one or more modifications within an Fc region that increases complement-dependent cytotoxicity (CDC). Such modifications include for example, IgG1-K326A, E333A; IgG1-K326W, E333S, IgG2-E333S (numbering according to Kabat EU index numbering system), and are known in the art (see, e.g. Idusogie et al., J. Immunol. 166:2571-2575 (2001); Strohl, Curr. Op. Biotechnol. 20:685-691 (2009); and Natsume et al., Cancer Res. 68:3863-3872 (2008), the contents of each of which is herein incorporated by reference in its entirety).

Suitable antibody proteins also include single chain antibodies. Also included are proteins comprising antibody fragments including Fc, Fab, Fab2, scFv fragments and the like. In some embodiments, the antibody protein is a fusion protein comprising a fragment of an immunoglobulin molecule. In some embodiments, the antibody protein is an Fc fusion protein (e.g. etanercept, abatacept, belatacept, alefacept, aflibercept, rilonacept, or luspatercept). Also embraced are single domain antibodies including nanobodies.

In certain embodiments, the antibody is fused or conjugated to an active molecule, such as a toxin or a chelating agent capable of binding a radioactive metal ion, such as $^{99}$Tc, $^{111}$Ir, $^{131}$I or $^{90}$Y (e.g. ibritumomab tiuxetan and tositumomab). In particular embodiments, the antibody is an antibody-drug conjugate (ADC) (e.g. gemtuzumab ozogamicin, brentuximab vedotin, trastuzumab emtansine, or inotuzumab ozogamicin). In such embodiments, the antibody typically functions as a targeting agent, for example, directing the active molecule to cells which display a certain cell surface protein.

Specific antibodies which can be formulated as described herein include, but are not limited to, infliximab (chimeric antibody, anti-TNFα), basiliximab (chimeric antibody, anti-IL-2), abciximab (chimeric antibody, anti-GpIIb/IIIa), daclizumab (humanized antibody, anti-IL-2), gemtuzumab (humanized antibody, anti-CD33), alemtuzumab (humanized antibody, anti-CD52), edrecolomab (murine Ig2a, anti-EpCAM), rituximab (chimeric antibody, anti-CD20), palivizumab (humanized antibody, anti-respiratory syncytial virus), trastuzumab (humanized antibody, anti-HER2/neu (erbB2) receptor), bevacizumab (humanized antibody, anti-VEGF), cetuximab (chimeric antibody, anti-EGFR), eculizumab (humanized antibody, anti-complement system protein C5), efalizumab (humanized antibody, anti-CD11a), ibritumomab (murine antibody, anti-CD20), muromonab-CD3 (murine antibody, anti-T cell CD3 receptor), natalizumab (humanized antibody, anti-α4 integrin), nimotuzumab (humanized IgG1, anti-EGF receptor), omalizumab (humanized antibody, anti-IgE), panitumumab (human antibody, anti-EGFR), ranibizumab (humanized antibody, anti-VEGF), $^{131}$I tositumomab (humanized antibody, anti-CD20), ofatumumab (human antibody, anti-CD-20), certolizumab (humanized antibody, anti-TNF-α), golimumab (human antibody, anti-TNF-α) and denosumab (human antibody, anti-RANK ligand). Preferred antibodies include trastuzumab, rituximab, bevacizumab, cetuximab and ipilimumab. In one embodiment, the monoclonal antibody is bevacizumab. In another embodiment, the monoclonal antibody is rituximab. In one embodiment, the antibody is not an anti-TNF-α antibody. In another embodiment, the antibody is an anti-TNF-α antibody. In a further embodiment, the monoclonal antibody is adalimumab.

Other chimeric antibodies which can be formulated as described herein include bavituximab (anti-phosphatidylserine), brentuximab (anti-CD30), siltuximab (anti-IL-6), clenoliximab (anti-CD4), galiximab (anti-CD80), gomiliximab (anti-CD23), keliximab (anti-CD4), lumiliximab (anti-CD23), priliximab (anti-CD4), teneliximab (anti-CD40), vapaliximab (anti-VAP1), ecromeximab (anti-GD3), and pagibaximab (anti-staphylococcal lipoteichoic acid).

Other humanized antibodies which can formulated as described herein include epratuzumab (anti-CD22), afutuzumab (anti-CD20), bivatuzumab mertansine (anti-CD44), cantuzumab mertansine (anti-mucin), citatuzumab bogatox (anti-TACSTD1), dacetuzumab (anti-CD40), elotuzumab (anti-CD319), etaracizumab (anti-αvβ3-integrin), farletuzumab (anti-FRα), inotuzumab ozogamicin (anti-CD22), labetuzumab (anti-carcinoembryonic antigen), lintuzumab (anti-CD33), milatuzumab (anti-CD74), nimotuzumab (anti-EGFR), oportuzumab monatox (anti-EpCAM), pertuzumab (anti-HER2), sibrotuzumab (anti-FAP), tacatuzumab tetraxetan (anti-alpha-fetoprotein), tigatuzumab (anti-TRAIL-2), tucotuzumab celmoleukin (anti-EpCAM), veltuzumab (anti-CD20), aselizumab (anti-CD62L), apolizumab (anti-HLA-DRB), benralizumab (anti-CD125), cedelizumab (anti-CD4), epratuzumab (anti-CD22), erlizumab (anti-CD18), fontolizumab (anti-interferon-γ), mepolizumab (anti-IL5), ocrelizumab (anti-CD20), pascolizumab (anti-IL4), pexelizumab (anti-complement component 5), PRO-140 (anti-CCR5), reslizumab (anti-IL5), rontalizumab (anti-interferon-α), rovelizumab (anti-CD11, CD18), siplizumab (anti-CD2), talizumab (anti-IgE), teplizumab (anti-CD3), tocilizumab (anti-IL6R), vedolizumab (anti-α4β7-integrin), visilizumab (anti-CD3), ibalizumab (anti-CD4), tefibazumab (anti-clumping factor A), tadocizumab (anti-α11bβ3-integrin), bapineuzumab (anti-amyloid-β), solanezumab (anti-amyloid-β), tanezumab (anti-NGF), urtoxazumab (anti-*E. coli* Shiga-like toxin II B subunit), felvizumab (anti-respiratory syncytial virus), motavizumab (anti-respiratory syncytial virus glycoprotein F) and lebrikizumab (anti-IL13).

Additional human antibodies which can be formulated as described herein include atorolimumab (anti-Rh factor), fresolimumab (anti-TGFβ-1, -2, and -3), lerdelimumab (anti-TGFβ-2), metelimumab (anti-TGF(3-1), morolimumab (anti-Rh factor), ipilimumab (anti-CTLA-4), tremelimumab (anti-CTLA-4), bertilimumab (anti-CCL11), zanolimumab (anti-CD4), briakinumab (anti-IL12, -23), canakinumab (anti-IL1β), ustekinumab (anti-IL12 and IL23), adecatumumab (anti-EpCAM), belimumab (anti-B cell activating factor), cixutumumab anti-IGF-1 receptor), conatumumab (anti-TRAIL-R2), figitumumab (anti-IGF-1 receptor), iratumumab (anti-CD30), lexatumumab (anti-TRAIL-R2), lucatumumab (anti-CD40), mapatumumab (anti-TRAIL-R4), necitumumab (anti-EGFR), olaratumab (anti-PDGF-Ra), pritumumab (anti-vimentin), robatumumab (anti-IGF-1 receptor), votumumab (anti-tumor antigen CTAA16.88), zalutumumab (anti-EGFR), stamulumab (anti-myostatin), efungumab (anti-fungal HSP90), exbivirumab (anti-hepatitis B surface antigen), foravirumab (anti-rabies glycoprotein), libivirumab (anti-hepatitis B surface antigen), rafivirumab (anti-rabies glycoprotein), regavirumab (anti-cytomegalovirus glycoprotein B), sevirumab (anti-cytomegalovirus), tuvirumab (anti-hepatitis B virus), panobacumab (anti-*Pseudomonas aeruginosa* serotype IATS 011), raxibacumab (anti-anthrax toxin), ramucirumab (anti-VEGF-R2), and gantenerumab (anti-amyloid-β).

Additional antibodies which can be formulated as described herein include obinutuzumab (humanized, anti-CD20), matuzumab (humanized, anti-EGFR), reslizumab (human, anti-IL5), dupilumab (human, anti-IL-4Rα), secukinumab (human, anti-IL-17A), brodalumab (human, anti-IL-17RA), dinutuximab (human anti-GD2), daratumumab (human, anti-CD38), bezlotoxumab (human, anti-*C. difficile* toxin B), obiltoxaximab (chimeric, anti-PA component of *B. anthracis* toxin), pavilizumab (humanized, anti-RSV F protein), atezolizumab (human, anti-PD-L1), avelumab (human, anti-PD-L1), durvalumab (human anti-PD-L1), pembrolizumab (human, anti-PD-1), nivolumab (human, anti-PD-1), idarucizumab (human Fab, anti-dabigatran), evolocumab (human, anti-PCSK9), and alirocumab (human, anti-PCSK9).

Adalimumab (human, anti-TNF-α) is an additional antibody that can be formulated as described herein.

Multispecific antibodies are also envisioned to be formulated as described herein. In some embodiments, the formulated antibody is bispecific. Bispecific antibodies that can be formulated as described herein include those that bind CD3 and another antigen (e.g. blinatumomab (CD3 and CD19) and anti-CD3 MUC1 bispecific antibodies). Additional bispecific antibodies that can be formulated as described herein include for example, ABT-981 (IL-1α and IL-1β), AFM13 (CD30 and CD16A), emicizumab (activated coagulation factor IX and factor X), istiratumab (IGF-1R and ErbB3), MEDI3902, ozoralizumab (TNF-alpha and HSA, RG7716 (VEGF and Ang-2), SAR156597 (IL-4 and IL-13) and vobarilizumab (anti-IL-6R).

ADCs which can be formulated as described herein include for example, gemtuzumab ozogamicin (humanized, anti-CD33), brentuximab vedotin (chimeric, anti-CD30), trastuzumab emtansine (humanized, anti-HER2), and inotuzumab ozogamicin (humanized, anti CD22).

Fusion proteins comprising a fragment of an immunoglobulin molecule can also be formulated according to the invention. Suitable fusion proteins include proteins comprising an active protein domain fused to one or more immunoglobulin fragments, such as Fc domains. Such fusion proteins include dimeric proteins having monomeric units comprising an active protein domain, such as a soluble receptor or a receptor extracellular ligand binding domain, which is fused to an immunoglobulin Fc domain. Two Fc domains can associate via disulfide bonds to form the dimeric protein. Such fusion proteins include for example, etanercept, abatacept and belatacept. Additional fusion proteins which can be formulated as described herein include for example, alefacept, aflibercept, rilonacept, romiplostim, eloctate, luspatercept, and alprolix.

Conjugated derivatives comprising antibodies (or one or more antibody fragments) and a chemically inert polymer such as polyethylene glycol (PEG) can also be formulated according to the invention. Such derivatives include certolizumab pegol.

The antibody protein can be isolated from natural sources or can be a recombinant protein.

In certain embodiments, the antibody protein is substantially pure, that is, the composition comprises a single antibody protein and no substantial amount of any additional protein. In preferred embodiments, the antibody protein comprises at least 99%, preferably at least 99.5% and more preferably at least about 99.9% of the total protein content of the composition. In preferred embodiments, the antibody protein is sufficiently pure for use as in a pharmaceutical composition.

The antibody protein is preferably a therapeutic antibody protein. Such an antibody protein has a desirable therapeutic or prophylactic activity and is indicated for the treatment, inhibition or prevention of a disease or medical disorder.

In one embodiment, antibody protein is a monoclonal antibody such as trastuzumab, rituximab, bevacizumab, cetuximab and ipilimumab. In another embodiment, the antibody protein is an antibody derivative in which the antibody is fused or conjugated to an active molecule such as a toxin or chelating agent (e.g. an ADC such as emtuzumab ozogamicin, brentuximab vedotin, trastuzumab emtansine, or inotuzumab ozogamicin). In one embodiment, the antibody protein is a monoclonal antibody such as infliximab. In another embodiment, the antibody protein is a fusion protein comprising an active protein domain fused to one or more immunoglobulin Fc fragments such as etanercept, abatacept or belatacept. In a further embodiment, the antibody is a derivative of an antibody protein and is a conjugated derivative comprising one or more antibodies or antibody fragments and a chemically inert polymer, such as polyethylene glycol (e.g. certolizumab pegol).

The antibody protein is suitably present at a concentration of about 1 mg/mL to about 300 mg/mL, such as about 10 mg/mL to about 300 mg/mL, about 1 mg/mL to about 200 mg/mL or about 10 mg/mL to about 200 mg/mL. In some embodiments, the antibody protein is present at a concentration of about 25 mg/mL to about 75 mg/mL. In some embodiments, the antibody protein is present at a concentration of about, about 80 mg/mL to about 125. In some embodiments, the antibody protein is present at a concentration of about 130 mg/mL to about 180 mg/mL. In some embodiments, the antibody protein is present at a concentration of about 190 mg/mL to about 250 mg/mL. In some embodiments, the antibody protein is present at a concentration of about 50 mg/mL. In some embodiments, the antibody protein is present at a concentration of about 75 mg/mL. In some embodiments, the antibody protein is present at a concentration of about 100 mg/mL. In some embodiments, the antibody protein is present at a concentration of about 125 mg/mL. In some embodiments, the antibody protein is present at a concentration of about 150 mg/mL. In some embodiments, the antibody protein is present at a concentration of about 160 mg/mL. In some embodiments, the antibody protein is present at a concentration of about 175 mg/mL. In some embodiments, the antibody protein is present at a concentration of about 200 mg/mL. In some embodiments, the antibody protein is present at a concentration of about 225 mg/mL. In some embodiments, the antibody protein is present at a concentration of about 240 mg/mL.

The aqueous solution of the present invention comprises arginine, suitably L-arginine. The arginine can be added to the aqueous solution in the form of a free base or in the form of a salt such as arginine hydrochloride. The arginine has a stabilizing effect (particularly with respect to reducing aggregation) and is typically present in the aqueous solution at a concentration of about 5 mM to about 100 mM, such as about 20 mM to about 80 mM, e.g. about 60 mM or about 80 mM.

The aqueous solution of the present invention also comprises methionine, suitably L-methionine. The methionine can be added to the aqueous solution in the form of a free base or in the form of a salt such as methionine hydrochloride. The methionine has a stabilizing effect (particularly with respect to reducing aggregation) and is typically present in the aqueous solution at a concentration of about 2 mM to about 50 mM, such as about 10 mM to about 40 mM, e.g. about 30 mM.

Typically, the pH of the aqueous solution of the present invention is between about pH 4.0 and about pH 8.0, such as between about pH 5.0 and about pH 7.0 or between about pH 5.0 and about pH 6.5.

In one embodiment, the aqueous solution of the invention further comprises a buffer in order to stabilise the pH of the formulation, which can also be selected to enhance antibody protein stability. While arginine and methionine may have buffering capacity, they typically do not act as buffers at in the pH range of between about pH 4.0 and about pH 8.0, which is a suitable pH range for the present aqueous solution. Hence, the aqueous solution may further comprise a buffer which is other than arginine or methionine.

Suitably the buffer is selected from the group consisting of histidine, succinate, maleate, acetate, phosphate and TRIS. In an embodiment, the buffer is phosphate. In a further embodiment, the buffer is citrate e.g. trisodium citrate. In a further embodiment, the buffer is acetate e.g. sodium acetate.

In one embodiment, a buffer is selected to have a pKa close to the pH of the composition; for example, histidine is suitably employed as a buffer when the pH of the composition is in the range 5.0-7.0. As another example, phosphate is suitably employed as a buffer when the pH of the composition is in the range 6.1-8.1. Alternatively, in another embodiment, the solution of the invention is further stabilised as disclosed in WO2008/084237A2, which describes a formulation comprising a protein and one or more additives, characterised in that the system is substantially free of a conventional buffer, i.e. a compound with an ionisable group having a pKa within 1 unit of the pH of the formulation at the intended temperature range of storage of the composition, such as 25° C. In this embodiment, the pH of the formulation is set to a value at which the formulation has maximum measurable stability with respect to pH; the one or more additives (displaced buffers) are capable of exchanging protons with the insulin compound and have pKa values at least 1 unit more or less than the pH of the formulation at the intended temperature range of storage of the formulation. The additives may have ionisable groups having pKa between 1 to 5 pH units of the pH of the formulation at the intended temperature range of storage of the composition (e.g. 25° C.). Preferably the additives have ionisable groups having pKa between 1 to 3 pH units, most preferably from 1.5 to 2.5 pH units, of the pH of the aqueous formulation at the intended temperature range of storage of the composition (e.g. 25° C.). Such additives may typically be employed at a concentration of about 0.5 mM to about 10 mM, e.g. about 2 mM to about 5 mM. In some embodiments, that additives are at a concentration of about 5 mM, about 8 mM, or about 10 mM.

Typically, the buffer is present at a concentration of about 0.5 mM to about 50 mM, such as about 1 mM to about 20 mM, e.g. about 2 mM to about 5 mM.

The aqueous solutions of the invention may optionally comprise a surfactant. In one embodiment, the surfactant is a non-ionic surfactant such as an alkyl glycoside e.g. dodecyl maltoside; a polysorbate surfactant such as polysorbate 80 or polysorbate 20; an alkyl ether of polyethylene glycol e.g. selected from polyethylene glycol (2) dodecyl ether, polyethylene glycol (2) oleyl ether and polyethylene glycol (2) hexadecyl ether; a block copolymer of polyethylene glycol and polypropylene glycol, such as poloxamer 188, poloxamer 407, poloxamer 171 or poloxamer 185; or an alkylphenyl ether of polyethylene glycol, such as 4-(1,1,3,3-tetramethylbutyl)phenyl-polyethylene glycol. Suitably the non-ionic surfactant is present at a concentration of about 10 µg/mL to about 2000 µg/mL, such as about 50 µg/mL to about 1000 µg/mL, e.g. about 100 µg/mL to about 500 µg/mL.

The aqueous solution of the invention may cover a wide range of osmolarity, including hypotonic, isotonic and hypertonic aqueous solutions. Suitably, the aqueous solution of the invention is substantially isotonic. In one embodiment, the aqueous solution of the invention is isotonic. Suitably, the osmolarity of the aqueous solution is selected to minimize pain according to the route of administration e.g. upon injection. Preferred aqueous solutions have an osmolarity in the range of about 200 mOsm/L to about 500 mOsm/L. Preferably, the osmolarity is in the range of about 250 mOsm/L to about 350 mOsm/L. More preferably, the osmolarity is about 300 mOsm/L.

Tonicity of the aqueous solution may be adjusted with a tonicity modifier. Tonicity modifiers may be charged or uncharged.

Examples of charged tonicity modifiers include salts such as a combination of sodium, potassium, magnesium or calcium ions, with chloride, sulfate, carbonate, sulfite, nitrate, lactate, succinate, acetate or maleate ions (especially sodium chloride or sodium sulphate, particularly sodium chloride). Amino acids such as glycine or histidine may also be used for this purpose. In one embodiment, the charged tonicity modifier is selected from the group consisting of sodium chloride, sodium sulphate, sodium acetate, sodium lactate, glycine and histidine. Arginine and methionine (both required components of the aqueous solution of the invention) may function as a charged tonicity modifier. However, reference to an aqueous solution of the invention "further" comprising a charged tonicity modifier is intended to refer to an additional, further component to be added to the solution. Thus, the aqueous solution may further comprise a charged tonicity modifier which is other than arginine or methionine. Such a charged tonicity modifier is typically present at a concentration of about 25 mM to about 500 mM, such as about 50 mM to about 250 mM, e.g. about 150 mM.

Examples of uncharged tonicity modifiers include sugars, sugar alcohols and other polyols, such as sucrose, trehalose, mannitol, raffinose, lactose, dextrose, sorbitol or lactitol, or polyethylene glycols such as PEG300 or PEG400. In one embodiment, the uncharged tonicity modifier is sucrose, trehalose, mannitol, sorbitol, PEG300 or PEG400. The C3 polyol which is a required component of the aqueous solution of the invention may function as an uncharged tonicity modifier. However, reference to an aqueous solution of the invention "further" comprising an uncharged tonicity modifier is intended to refer to an additional, further component to be added to the solution. Thus, the aqueous solution may further comprise an uncharged tonicity modifier which is other than a C3 polyol, and in particular is other than 1,2-propanediol and glycerol. Such an uncharged tonicity modifier is typically present at a concentration of about 50 mM to about 1000 mM, such as about 100 mM to about 500 mM, e.g. about 300 mM.

The aqueous solution of the invention can optionally include a preservative, suitably selected from phenol, m-cresol, chlorocresol, benzyl alcohol, propylparaben, methylparaben, benzalkonium chloride and benzethonium chloride. When present, the preservative is at a concentration of about 0.01 mM to about 100 mM. A preservative selected from phenol, m-cresol, chlorocresol, benzyl alcohol, propylparaben, methylparaben may, for example, be present at a concentration of about 10 mM to about 100 mM, such as about 20 mM to about 80 mM e.g. about 25 mM to about 50 mM. A preservative selected from benzalkonium chloride and benzethonium chloride may, for example, be present at a concentration of about 0.01 mM to about 1 mM such as about 0.05 mM to about 0.5 mM e.g. about 0.05 mM to about 0.2 mM.

In some embodiments, the disclosure provides:

[1] an aqueous solution comprising
  (i) an antibody protein, and
  (ii) a stabilizing amount of arginine, methionine and a C3 polyol;
[2] a method of stabilizing an antibody protein in an aqueous solution comprising the step of adding to the solution arginine, methionine and a C3 polyol;
[3] use of arginine, methionine and a C3 polyol for stabilizing an antibody protein in an aqueous solution to storage;
[4] the aqueous solution of [1], method of [2], or use of [3], wherein the C3 polyol is 1,2-propanediol;
[5] the aqueous solution of [1], method of [2], or use of [3], wherein the C3 polyol is glycerol;
[6] the aqueous solution of [1], method of [2], or use of [3], wherein the C3 polyol is a mixture of 1,2-propanediol and glycerol;
[7] the aqueous solution, method or use of any one of [1] to [6], wherein the C3 polyol is present at a concentration of about 100 mM to about 500 mM, such as about 150 mM to about 400 mM, or about 150 mM to about 200 mM;
[8] the aqueous solution, method or use of any one of [1] to [7], wherein the antibody protein is a therapeutic antibody protein;
[9] the aqueous solution, method or use of any one of [1] to [8], wherein the antibody protein is an antibody, an antibody fragment, an antibody conjugated to an active moiety, a fusion protein comprising one or more antibody fragments, or a derivative of any of the aforementioned;
[10] the aqueous solution, method or use of [9], wherein the antibody protein is a monoclonal antibody;

[11] the aqueous solution, method or use of [10], wherein the monoclonal antibody is a murine antibody, a chimeric antibody, a humanized antibody or a human antibody;

[12] the aqueous solution, method or use of [11], wherein the monoclonal antibody is selected from trastuzumab, rituximab, bevacizumab, cetuximab and ipilimumab;

[13] the aqueous solution, method or use of [11], wherein the monoclonal antibody is rituximab or bevacizumab, or adalimumab;

[14] the aqueous solution, method or use of [9], wherein the antibody protein is a fusion protein comprising an active protein domain fused to one or more immunoglobulin Fc fragments;

[15] the aqueous solution, method or use of [14], wherein the antibody protein is etanercept, abatacept or belatacept;

[16] the aqueous solution, method or use of [9], wherein the derivative is a conjugated derivative comprising one or more antibodies or antibody fragments and a chemically inert polymer;

[17] the aqueous solution, method or use of [16], wherein the conjugated derivative is a certolizumab pegol;

[18] the aqueous solution, method or use of any one of [1] to [17], wherein the antibody protein is present at a concentration of about 1 mg/mL to about 300 mg/mL (e.g. about 10 mg/mL to about 300 mg/mL, about 1 mg/mL to about 200 mg/mL, about 10 mg/mL to about 200 mg/mL, about 25 mg/mL to about 75 mg/mL, about 80 mg/mL to about 125, about 130 mg/mL to about 180 mg/mL, or about 190 mg/mL to about 250 mg/mL, or about 50 mg/mL, about 100 mg/mL, about 150 mg/mL, about 160 mg/mL, about 200 mg/mL, or about 240 mg/mL), optionally, wherein the antibody protein is rituximab, bevacizumab, or adalimumab;

[19] the aqueous solution, method or use of any one of [1] to [18], wherein the arginine is present at a concentration of about 5 mM to about 100 mM, such as about 20 mM to about 80 mM, e.g. about 60 mM;

[20] the aqueous solution, method or use of any one of [1] to [19], wherein the methionine is present at a concentration of about 2 mM to about 50 mM, such as about 10 mM to about 40 mM, e.g. about 30 mM;

[21] the aqueous solution, method or use of any one of [1] to [20], wherein the pH of the solution is between about pH 4.0 and about pH 8.0, such as between about pH 5.0 and about pH 7.0, or between about pH 5.0 and about pH 6.5;

[22] the aqueous solution, method or use of any one of [1] to [21], further comprising a buffer;

[23] the aqueous solution, method or use of [22], wherein the buffer is selected from the group consisting of histidine, succinate, maleate, acetate, phosphate and TRIS;

[24] the aqueous solution, method or use of [22] or [23], wherein the buffer is present at a concentration of about 0.5 mM to about 50 mM, such as about 1 mM to about 20 mM, e.g. about 2 mM to about 5 mM;

[25] the aqueous solution, method or use of any one of [1] to [24], further comprising a non-ionic surfactant;

[26] the aqueous solution, method or use of [25], wherein the non-ionic surfactant is an alkyl glycoside, such as dodecyl maltoside;

[27] the aqueous solution, method or use of [25], wherein the non-ionic surfactant is a polysorbate surfactant, such as polysorbate 80 or polysorbate 20;

[28] the aqueous solution, method or use of [25], wherein the non-ionic surfactant is an alkyl ether of polyethylene glycol;

[29] the aqueous solution, method or use of [28], wherein the alkyl ether of polyethylene glycol is selected from polyethylene glycol (2) dodecyl ether, polyethylene glycol (2) oleyl ether and polyethylene glycol (2) hexadecyl ether;

[30] the aqueous solution, method or use of [25], wherein the non-ionic surfactant is a block copolymer of polyethylene glycol and polypropylene glycol, such as poloxamer 188, poloxamer 407, poloxamer 171 or poloxamer 185;

[31] the aqueous solution, method or use of [25], wherein the non-ionic surfactant is an alkylphenyl ether of polyethylene glycol, such as 4-(1,1,3,3-tetramethylbutyl) phenyl-polyethylene glycol;

[32] the aqueous solution, method or use of any one of [25] to [31], wherein the non-ionic surfactant is present at a concentration of about 10 μg/mL to about 2000 μg/mL, such as about 50 μg/mL to about 1000 μg/mL, e.g. about 100 μg/mL to about 500 μg/mL;

[33] the aqueous solution, method or use of any one of [1] to [32], further comprising an uncharged tonicity modifier, such as sucrose, trehalose, mannitol, sorbitol, PEG300 or PEG400;

[34] the aqueous solution, method or use of [33], wherein the uncharged tonicity modifier is present at a concentration of about 50 mM to about 1000 mM, such as about 100 mM to about 500 mM, e.g. about 300 mM;

[35] the aqueous solution, method or use of any one of [1] to [34], further comprising a charged tonicity modifier, such as selected from the group consisting of sodium chloride, sodium sulphate, sodium acetate, sodium lactate, glycine and histidine;

[36] the aqueous solution, method or use of [35], wherein the charged tonicity modifier is present at a concentration of about 25 mM to about 500 mM, such as about 50 mM to about 250 mM, e.g. about 150 mM;

[37] the aqueous solution, method or use of any one of [1] to [36], wherein the aqueous solution is isotonic;

[38] the aqueous solution, method or use of any of [1] to [37], further comprising a preservative;

[39] the aqueous solution, method or use of [38], wherein the preservative is selected from the group consisting of phenol, m-cresol, chlorocresol, benzyl alcohol, propylparaben, methylparaben, benzalkonium chloride and benzethonium chloride;

[40] the aqueous solution, method or use of [38] or [39], wherein the preservative is present at a concentration of about 0.01 mM to about 100 mM;

[41] the method of [2], or of any one of [4] to [40], wherein the method for stabilizing the antibody protein is a method for inhibiting formation of high molecular weight species of the antibody protein during storage;

[42] the method of [2], or of any one of [4] to [40], wherein the method of stabilizing the antibody protein is a method for inhibiting formation of related species of the antibody protein during storage;

[43] the method of [2], or of any one of [4] to [40], wherein the method of stabilizing the antibody protein is a method for inhibiting deamidation of the antibody protein during storage;

[44] the method of [2], or of any one of [4] to [40], wherein the method of stabilizing the antibody protein is a method for inhibiting formation of low molecular weight degradation products of the antibody protein during storage;

[45] the method of [2], or of any one of [4] to [40], wherein the method of stabilizing the antibody protein is a method for inhibiting formation of visible particles in an aqueous solution of the antibody protein during storage;

[46] the use of any one of [3] to [40], for inhibiting formation of high molecular weight species of the antibody protein during storage;

[47] the use of any one of [3] to [40], for inhibiting formation of related species of the antibody protein during storage;

[48] the use of any one of [3] to [40], for inhibiting deamidation of the antibody protein during storage;

[49] the use of any one of [3] to [40], for inhibiting formation of low molecular weight degradation products of the antibody protein during storage;

[50] the use of any one of [3] to [40], for inhibiting formation of visible particles in an aqueous solution of the antibody protein during storage; or

[51] the aqueous solution of [1] or of any one of [4] to [40], wherein the solution is for administration by subcutaneous or intramuscular injection or by intravenous injection or infusion.

In some embodiments, the aqueous solution of the invention comprises, (a) an antibody protein (e.g. a type of, or specific therapeutic antibody protein described herein such as a monoclonal antibody, multispecific antibody (e.g. a bispecific antibody), ADC, conjugated antibody derivative, or a fusion protein such as an Fc fusion protein) at a concentration of about 1 mg/mL to about 300 mg/mL (e.g. about 10 mg/mL to about 300 mg/mL, about 1 mg/mL to about 200 mg/mL, about 10 mg/mL to about 200 mg/mL, about 25 mg/mL to about 75 mg/mL, about 80 mg/mL to about 125, about 130 mg/mL to about 180 mg/mL, or about 190 mg/mL to about 250 mg/mL, or about 50 mg/mL, about 100 mg/mL, about 150 mg/mL, about 160 mg/mL, about 200 mg/mL, or about 240 mg/mL); and (b) a stabilizing amount of
  (i) 1,2-propanediol or glycerol, or a mixture thereof, at a concentration of about 100 mM to about 500 mM (e.g. about 150 mM to about 400 mM, about 150 mM to about 350 mM, or about 200 mM to about 300 mM, or about 200 mg/mL, about 250 mg/mL, or about 300 mg/mL),
  (ii) arginine (e.g. L arginine) at a concentration of about 5 mM to about 150 mM, (e.g. about 5 mM to about 100 mM, about 20 mM to about 125 mM, about 60 mM to about 120 mM, about 60 mM to about 100 mM, or about 20 mM to about 80 mM, or about 50 mM, about 60 mM, about 80 mM, about 100 mM, or about 150 mM), and
  (iii) methionine (e.g. L methionine) at a concentration of 2 mM to about 75 mM (e.g. 2 mM to about 50 mM, or about 10 mM to about 40 mM, or about 30 mM); and
optionally, wherein the ratio (mM/mM) of arginine to methionine is between about 1:1 and about 10:1 (e.g. between about 2:1 and about 6:1), the ratio (mM/mM) of arginine to C3 polyol is between about 2:1 and 1:20 (e.g. between about 1:2 and about 1:10), the ratio (mM/mM) of methionine to C3 polyol is between about 1:1 and 1:40 (e.g. between about 1:4 and about 1:20), the ratio (mM/mM) of the combined concentration of arginine and methionine to C3 polyol is between about 4:1 and 1:20 (e.g. between about 2:1 and about 1:10), the ratio (wt/wt) of antibody protein to the combined weight of arginine and methionine is between about 1:15 and about 30:1 (e.g. between about 1:1 and about 25:1), or between about 1:2 and about 50:1 (e.g. between about 2:1 and about 25:1), and/or the ratio (wt/wt) of antibody protein to C3 polyol is between about 1:5 and about 200:1 (e.g. between about 2:1 and about 50:1) or between about 1:2 and about 200:1 (e.g. between about 2:1 and about 50:1);

wherein the pH of the aqueous solution is between about pH 4.0 and about pH 8.0 (e.g. between about pH 5.0 and about pH 7.0 or between about pH 5.0 and about pH 6.5);
optionally wherein the aqueous solution further comprises
  (i) a buffer (e.g. histidine, succinate, maleate, acetate, phosphate or TRIS) at a concentration of about 0.5 mM to about 50 mM (e.g. about 1 mM to about 20 mM, about 2 mM to about 10 mM, or about 2 mM to about 5 mM),
  (ii) a non-ionic surfactant (e.g. an alkyl glycoside, such as dodecyl maltoside, a polysorbate surfactant, such as polysorbate 80, or polysorbate 20, an alkyl ether of polyethylene glycol, such as polyethylene glycol (2) dodecyl ether, polyethylene glycol (2) oleyl ether or polyethylene glycol (2) hexadecyl ether, a block copolymer of polyethylene glycol and polypropylene glycol, such as poloxamer 188, poloxamer 407, poloxamer 171, or poloxamer 185, or an alkylphenyl ether of polyethylene glycol, such as 4-(1,1,3,3-tetramethylbutyl) phenyl-polyethylene glycol, at a concentration of about 10 µg/mL to about 2000 µg/mL (e.g. about 50 µg/mL to about 1500 µg/mL, about 50 µg/mL to about 1250 µg/mL, about 50 µg/mL to about 1000 µg/mL, about 100 µg/mL to about 750 µg/mL, or about 100 µg/mL to about 500 µg/mL, or about 500 µg/mL, about 750 µg/mL, about 1000 µg/mL, about 1250 µg/mL, or about 1500 µg/mL),
  (iii) a tonicity modifier (e.g. an uncharged tonicity modifier, such as sucrose, trehalose, mannitol, sorbitol, PEG300, or PEG400, at a concentration of about 50 mM to about 1000 mM, such as about 100 mM to about 500 mM), or a charged tonicity modifier such as sodium chloride, sodium sulphate, sodium acetate, sodium lactate, glycine, histidine, or arginine, at a concentration of about 25 mM to about 500 mM such as about 50 mM to about 250 mM, and/or
  (iv) a preservative such as phenol, m-cresol, chlorocresol, benzyl alcohol, propylparaben, methylparaben, benzalkonium chloride, or benzethonium chloride, at a concentration of about 0.01 mM to about 100 mM.

In some embodiments, the conductivity of the aqueous solution is >2.5 mS/cm. In some embodiments, the conductivity of the aqueous solution is <2.5 mS/cm.

In some embodiments, the aqueous solution of the invention comprises, (a) an IgG1 antibody (e.g. trastuzumab, rituximab, bevacizumab, cetuximab, adalimumab, infliximab, ipilimumab, avelumab, alirocumab, necitumumab, obinutuzumab, ofatumumab, olaratumab, palivizumab, ramucirumab, raxibacumab, sarilumab, secukinumab, or ustekinumab) at a concentration of about 1 mg/mL to about 300 mg/mL (e.g. about 10 mg/mL to about 300 mg/mL, about 1 mg/mL to about 200 mg/mL, about 10 mg/mL to about 200 mg/mL, about 25 mg/mL to about 75 mg/mL, about 80 mg/mL to about 125, about 130 mg/mL to about 180 mg/mL, or about 190 mg/mL to about 250 mg/mL, or about 50 mg/mL, about 100 mg/mL, about 150 mg/mL, about 160 mg/mL, about 200 mg/mL, or about 240 mg/mL); and (b) a stabilizing amount of
  (i) 1,2-propanediol or glycerol, or a mixture thereof, at a concentration of about 100 mM to about 500 mM (e.g. about 150 mM to about 400 mM, about 150 mM to about 350 mM, or about 200 mM to about 300 mM, or about 200 mg/mL, about 250 mg/mL, or about 300 mg/mL), (ii) arginine (e.g. L arginine) at a concentration of about 5 mM to about 150 mM, (e.g. about 5 mM to about 100 mM, about 20 mM to about 125 mM, about 60 mM to about 120 mM, about 60 mM to about 100 mM, or about 20 mM to about 80 mM, or about 50 mM, about 60 mM, about 80 mM, about 100 mM, or about 150 mM), and (iii) methionine (e.g. L methionine) at a concentration of 2 mM to about 75 mM (e.g. 2 mM to about 50 mM, or about 10 mM to about 40 mM, or about 30 mM);

optionally, wherein the ratio (mM/mM) of arginine to methionine is between about 1:1 and about 10:1 (e.g. between about 2:1 and about 6:1), the ratio (mM/mM) of arginine to C3 polyol is between about 2:1 and 1:20 (e.g. between about 1:2 and about 1:10), the ratio (mM/mM) of methionine to C3 polyol is between about 1:1 and 1:40 (e.g. between about 1:4 and about 1:20), the ratio (mM/mM) of the combined concentration of arginine and methionine to C3 polyol is between about 4:1 and 1:20 (e.g. between about 2:1 and about 1:10), the ratio (wt/wt) of antibody protein to the combined weight of arginine and methionine is between about 1:15 and about 30:1 (e.g. between about 1:1 and about 25:1), or between about 1:2 and about 50:1 (e.g. between about 2:1 and about 25:1), and/or the ratio (wt/wt) of antibody protein to C3 polyol is between about 1:5 and about 200:1 (e.g. between about 2:1 and about 50:1) or between about 1:2 and about 200:1 (e.g. between about 2:1 and about 50:1); and wherein the pH of the aqueous solution is between about pH 4.0 and about pH 8.0 (e.g. between about pH 5.0 and about pH 7.0 or between about pH 5.0 and about pH 6.5); optionally wherein the aqueous solution further comprises (i) a buffer (e.g. histidine, succinate, maleate, acetate, phosphate or TRIS) at a concentration of about 0.5 mM to about 50 mM (e.g. about 1 mM to about 20 mM, about 2 mM to about 10 mM, or about 2 mM to about 5 mM), (ii) a non-ionic surfactant (e.g. an alkyl glycoside, such as dodecyl maltoside, a polysorbate surfactant, such as polysorbate 80, or polysorbate 20, an alkyl ether of polyethylene glycol, such as polyethylene glycol (2) dodecyl ether, polyethylene glycol (2) oleyl ether or polyethylene glycol (2) hexadecyl ether, a block copolymer of polyethylene glycol and polypropylene glycol, such as poloxamer 188, poloxamer 407, poloxamer 171, or poloxamer 185, or an alkylphenyl ether of polyethylene glycol, such as 4-(1,1,3,3-tetramethylbutyl) phenyl-polyethylene glycol, at a concentration of about 10 μg/mL to about 2000 μg/mL (e.g. about 50 μg/mL to about 1500 μg/mL, about 50 μg/mL to about 1250 μg/mL, about 50 μg/mL to about 1000 μg/mL, about 100 μg/mL to about 750 μg/mL, or about 100 μg/mL to about 500 μg/mL, or about 500 μg/mL, about 750 μg/mL, about 1000 μg/mL, about 1250 μg/mL, or about 1500 μg/mL), (iii) a tonicity modifier (e.g. an uncharged tonicity modifier, such as sucrose, trehalose, mannitol, sorbitol, PEG300, or PEG400, at a concentration of about 50 mM to about 1000 mM, such as about 100 mM to about 500 mM), or a charged tonicity modifier such as sodium chloride, sodium sulphate, sodium acetate, sodium lactate, glycine, histidine, or arginine, at a concentration of about 25 mM to about 500 mM such as about 50 mM to about 250 mM, and/or (iv) a preservative such as phenol, m-cresol, chlorocresol, benzyl alcohol, propylparaben, methylparaben, benzalkonium chloride, or benzethonium chloride, at a concentration of about 0.01 mM to about 100 mM.

In some embodiments, the conductivity of the aqueous solution is >2.5 mS/cm. In some embodiments, the conductivity of the aqueous solution is <2.5 mS/cm.

In some embodiments, the aqueous solution of the invention comprises, (a) an IgG2 antibody (e.g. evolocumab, eculizumab, panitumumab, denosumab, or brodalumab) at a concentration of about 1 mg/mL to about 300 mg/mL (e.g. about 10 mg/mL to about 300 mg/mL, about 1 mg/mL to about 200 mg/mL, about 10 mg/mL to about 200 mg/mL, about 25 mg/mL to about 75 mg/mL, about 80 mg/mL to about 125, about 130 mg/mL to about 180 mg/mL, or about 190 mg/mL to about 250 mg/mL, or about 50 mg/mL, about 100 mg/mL, about 150 mg/mL, about 160 mg/mL, about 200 mg/mL, or about 240 mg/mL); and (b) a stabilizing amount of (i) 1,2-propanediol or glycerol, or a mixture thereof, at a concentration of about 100 mM to about 500 mM (e.g. about 150 mM to about 400 mM, about 150 mM to about 350 mM, or about 200 mM to about 300 mM, or about 200 mg/mL, about 250 mg/mL, or about 300 mg/mL), (ii) arginine (e.g. L arginine) at a concentration of about 5 mM to about 150 mM, (e.g. about 5 mM to about 100 mM, about 20 mM to about 125 mM, about 60 mM to about 120 mM, about 60 mM to about 100 mM, or about 20 mM to about 80 mM, or about 50 mM, about 60 mM, about 80 mM, about 100 mM, or about 150 mM), and (iii) methionine (e.g. L methionine) at a concentration of 2 mM to about 75 mM (e.g. 2 mM to about 50 mM, or about 10 mM to about 40 mM, or about 30 mM);

optionally, wherein the ratio (mM/mM) of arginine to methionine is between about 1:1 and about 10:1 (e.g. between about 2:1 and about 6:1), the ratio (mM/mM) of arginine to C3 polyol is between about 2:1 and 1:20 (e.g. between about 1:2 and about 1:10), the ratio (mM/mM) of methionine to C3 polyol is between about 1:1 and 1:40 (e.g. between about 1:4 and about 1:20), the ratio (mM/mM) of the combined concentration of arginine and methionine to C3 polyol is between about 4:1 and 1:20 (e.g. between about 2:1 and about 1:10), the ratio (wt/wt) of antibody protein to the combined weight of arginine and methionine is between about 1:15 and about 30:1 (e.g. between about 1:1 and about 25:1), or between about 1:2 and about 50:1 (e.g. between about 2:1 and about 25:1), and/or the ratio (wt/wt) of antibody protein to C3 polyol is between about 1:5 and about 200:1 (e.g. between about 2:1 and about 50:1) or between about 1:2 and about 200:1 (e.g. between about 2:1 and about 50:1); and wherein the pH of the aqueous solution is between about pH 4.0 and about pH 8.0 (e.g. between about pH 5.0 and about pH 7.0 or between about pH 5.0 and about pH 6.5); optionally wherein the aqueous solution further comprises (i) a buffer (e.g. histidine, succinate, maleate, acetate, phosphate or TRIS) at a concentration of about 0.5 mM to about 50 mM (e.g. about 1 mM to about 20 mM, about 2 mM to about 10 mM, or about 2 mM to about 5 mM), (ii) a non-ionic surfactant (e.g. an alkyl glycoside, such as dodecyl maltoside, a polysorbate surfactant, such as polysorbate 80, or polysorbate 20, an alkyl ether of polyethylene glycol, such as polyethylene glycol (2) dodecyl ether, polyethylene glycol (2) oleyl ether or polyethylene glycol (2) hexadecyl ether, a block copolymer of polyethylene glycol and polypropylene glycol, such as poloxamer 188, poloxamer 407, poloxamer 171, or poloxamer 185, or an alkylphenyl ether of polyethylene glycol, such as 4-(1,1,3,3-tetramethylbutyl) phenyl-polyethylene glycol, at a concentration of about 10 µg/mL to about 2000 µg/mL (e.g. about 50 µg/mL to about 1500 µg/mL, about 50 µg/mL to about 1250 µg/mL, about 50 µg/mL to about 1000 µg/mL, about 100 µg/mL to about 750 µg/mL, or about 100 µg/mL to about 500 µg/mL, or about 500 µg/mL, about 750 µg/mL, about 1000 µg/mL, about 1250 µg/mL, or about 1500 µg/mL),
(iii) a tonicity modifier (e.g. an uncharged tonicity modifier, such as sucrose, trehalose, mannitol, sorbitol, PEG300, or PEG400, at a concentration of about 50 mM to about 1000 mM, such as about 100 mM to about 500 mM), or a charged tonicity modifier such as sodium chloride, sodium sulphate, sodium acetate, sodium lactate, glycine, histidine, or arginine, at a concentration of about 25 mM to about 500 mM such as about 50 mM to about 250 mM, and/or
(iv) a preservative such as phenol, m-cresol, chlorocresol, benzyl alcohol, propylparaben, methylparaben, benzalkonium chloride, or benzethonium chloride, at a concentration of about 0.01 mM to about 100 mM.

In some embodiments, the conductivity of the aqueous solution is >2.5 mS/cm. In some embodiments, the conductivity of the aqueous solution is <2.5 mS/cm.

In some embodiments, the aqueous solution of the invention comprises,
(a) an IgG4 antibody (e.g. pembroluzumab, nivolumab or dupilumab) at a concentration of about 1 mg/mL to about 300 mg/mL (e.g. about 10 mg/mL to about 300 mg/mL, about 1 mg/mL to about 200 mg/mL, about 10 mg/mL to about 200 mg/mL, about 25 mg/mL to about 75 mg/mL, about 80 mg/mL to about 125, about 130 mg/mL to about 180 mg/mL, or about 190 mg/mL to about 250 mg/mL, or about 50 mg/mL, about 100 mg/mL, about 150 mg/mL, about 160 mg/mL, about 200 mg/mL, or about 240 mg/mL); and
(b) a stabilizing amount of
  (i) 1,2-propanediol or glycerol, or a mixture thereof, at a concentration of about 100 mM to about 500 mM (e.g. about 150 mM to about 400 mM, about 150 mM to about 350 mM, or about 200 mM to about 300 mM, or about 200 mg/mL, about 250 mg/mL, or about 300 mg/mL),
  (ii) arginine (e.g. L arginine) at a concentration of about 5 mM to about 150 mM, (e.g. about 5 mM to about 100 mM, about 20 mM to about 125 mM, about 60 mM to about 120 mM, about 60 mM or about 100 mM, or about 20 mM to about 80 mM, or about 50 mM, about 60 mM, about 80 mM, about 100 mM, or about 150 mM), and
  (iii) methionine (e.g. L methionine) at a concentration of 2 mM to about 75 mM (e.g. 2 mM to about 50 mM, or about 10 mM to about 40 mM, or about 30 mM);
  optionally, wherein the ratio (mM/mM) of arginine to methionine is between about 1:1 and about 10:1 (e.g. between about 2:1 and about 6:1), the ratio (mM/mM) of arginine to C3 polyol is between about 2:1 and 1:20 (e.g. between about 1:2 and about 1:10), the ratio (mM/mM) of methionine to C3 polyol is between about 1:1 and 1:40 (e.g. between about 1:4 and about 1:20), the ratio (mM/mM) of the combined concentration of arginine and methionine to C3 polyol is between about 4:1 and 1:20 (e.g. between about 2:1 and about 1:10), the ratio (wt/wt) of antibody protein to the combined weight of arginine and methionine is between about 1:15 and about 30:1 (e.g. between about 1:1 and about 25:1), or between about 1:2 and about 50:1 (e.g. between about 2:1 and about 25:1), and/or the ratio (wt/wt) of antibody protein to C3 polyol is between about 1:5 and about 200:1 (e.g. between about 2:1 and about 50:1) or between about 1:2 and about 200:1 (e.g. between about 2:1 and about 50:1); and
wherein the pH of the aqueous solution is between about pH 4.0 and about pH 8.0 (e.g. between about pH 5.0 and about pH 7.0 or between about pH 5.0 and about pH 6.5);
optionally wherein the aqueous solution further comprises
  (i) a buffer (e.g. histidine, succinate, maleate, acetate, phosphate or TRIS) at a concentration of about 0.5 mM to about 50 mM (e.g. about 1 mM to about 20 mM, about 2 mM to about 10 mM, or about 2 mM to about 5 mM),
  (ii) a non-ionic surfactant (e.g. an alkyl glycoside, such as dodecyl maltoside, a polysorbate surfactant, such as polysorbate 80, or polysorbate 20, an alkyl ether of polyethylene glycol, such as polyethylene glycol (2) dodecyl ether, polyethylene glycol (2) oleyl ether or polyethylene glycol (2) hexadecyl ether, a block copolymer of polyethylene glycol and polypropylene glycol, such as poloxamer 188, poloxamer 407, poloxamer 171, or poloxamer 185, or an alkylphenyl ether of polyethylene glycol, such as 4-(1,1,3,3-tetramethylbutyl) phenyl-polyethylene glycol, at a concentration of about 10 µg/mL to about 2000 µg/mL (e.g. about 50 µg/mL to about 1500 µg/mL, about 50 µg/mL to about 1250 µg/mL, about 50 µg/mL to about 1000 µg/mL, about 100 µg/mL to about 750 µg/mL, or about 100 µg/mL to about 500 µg/mL, or about 500 µg/mL, about 750 µg/mL, about 1000 µg/mL, about 1250 µg/mL, or about 1500 µg/mL),
  (iii) a tonicity modifier (e.g. an uncharged tonicity modifier, such as sucrose, trehalose, mannitol, sorbitol, PEG300, or PEG400, at a concentration of about 50 mM to about 1000 mM, such as about 100 mM to about 500 mM), or a charged tonicity modifier such as sodium chloride, sodium sulphate, sodium acetate, sodium lactate, glycine, histidine, or arginine, at a concentration of about 25 mM to about 500 mM such as about 50 mM to about 250 mM, and/or
  (iv) a preservative such as phenol, m-cresol, chlorocresol, benzyl alcohol, propylparaben, methylparaben, benzalkonium chloride, or benzethonium chloride, at a concentration of about 0.01 mM to about 100 mM.

In some embodiments, the conductivity of the aqueous solution is >2.5 mS/cm. In some embodiments, the conductivity of the aqueous solution is <2.5 mS/cm.

In some embodiments, the aqueous solution of the invention comprises,
(a) adalimumab at a concentration of about 1 mg/mL to about 300 mg/mL (e.g. about 10 mg/mL to about 300 mg/mL, about 1 mg/mL to about 200 mg/mL, about 10 mg/mL to about 200 mg/mL, about 25 mg/mL to about 75 mg/mL, about 80 mg/mL to about 125, about 130 mg/mL to about 180 mg/mL, or about 190 mg/mL to about 250 mg/mL, or about 50 mg/mL, about 100 mg/mL, about 150 mg/mL, about 160 mg/mL, about 200 mg/mL, or about 240 mg/mL); and
(b) a stabilizing amount of
  (i) 1,2-propanediol or glycerol, or a mixture thereof at a concentration of about 100 mM to about 500 mM (e.g. about 150 mM to about 400 mM, about 150 mM to about 350 mM, or about 200 mM to about 300 mM, or about 200 mg/mL, about 250 mg/mL, or about 300 mg/mL),
(ii) arginine (e.g. L arginine) at a concentration of about 5 mM to about 150 mM, (e.g. about 5 mM to about 100 mM, about 20 mM to about 125 mM, about 60 mM to about 120 mM, about 60 mM to about 100 mM, or about 20 mM to about 80 mM, or about 50 mM, about 60 mM, about 80 mM, about 100 mM, or about 150 mM), and
(iii) methionine (e.g. L methionine) at a concentration of 2 mM to about 75 mM (e.g. 2 mM to about 50 mM, or about 10 mM to about 40 mM, or about 30 mM);
optionally, wherein the ratio (mM/mM) of arginine to methionine is between about 1:1 and about 10:1 (e.g. between about 2:1 and about 6:1), the ratio (mM/mM) of arginine to C3 polyol is between about 2:1 and 1:20 (e.g. between about 1:2 and about 1:10), the ratio (mM/mM) of methionine to C3 polyol is between about 1:1 and 1:40 (e.g. between about 1:4 and about 1:20), the ratio (mM/mM) of the combined concentration of arginine and methionine to C3 polyol is between about 4:1 and 1:20 (e.g. between about 2:1 and about 1:10), the ratio (wt/wt) of antibody protein to the combined weight of arginine and methionine is between about 1:15 and about 30:1 (e.g. between about 1:1 and about 25:1), or between about 1:2 and about 50:1 (e.g. between about 2:1 and about 25:1), and/or the ratio (wt/wt) of antibody protein to C3 polyol is between about 1:5 and about 200:1 (e.g. between about 2:1 and about 50:1) or between about 1:2 and about 200:1 (e.g. between about 2:1 and about 50:1); and
wherein the pH of the aqueous solution is between about pH 4.0 and about pH 8.0 (e.g. between about pH 5.0 and about pH 7.0 or between about pH 5.0 and about pH 6.5);
optionally wherein the aqueous solution further comprises
(i) a buffer (e.g. histidine, succinate, maleate, acetate, phosphate or TRIS) at a concentration of about 0.5 mM to about 50 mM (e.g. about 1 mM to about 20 mM, about 2 mM to about 10 mM, or about 2 mM to about 5 mM),
(ii) a non-ionic surfactant (e.g. an alkyl glycoside, such as dodecyl maltoside, a polysorbate surfactant, such as polysorbate 80, or polysorbate 20, an alkyl ether of polyethylene glycol, such as polyethylene glycol (2) dodecyl ether, polyethylene glycol (2) oleyl ether or polyethylene glycol (2) hexadecyl ether, a block copolymer of polyethylene glycol and polypropylene glycol, such as poloxamer 188, poloxamer 407, poloxamer 171, or poloxamer 185, or an alkylphenyl ether of polyethylene glycol, such as 4-(1,1,3,3-tetramethylbutyl) phenyl-polyethylene glycol, at a concentration of about 10 μg/mL to about 2000 μg/mL (e.g. about 50 μg/mL to about 1500 μg/mL, about 50 μg/mL to about 1250 μg/mL, about 50 μg/mL to about 1000 μg/mL, about 100 μg/mL to about 750 μg/mL, or about 100 μg/mL to about 500 μg/mL, or about 500 μg/mL, about 750 μg/mL, about 1000 μg/mL, about 1250 μg/mL, or about 1500 μg/mL),
(iii) a tonicity modifier (e.g. an uncharged tonicity modifier, such as sucrose, trehalose, mannitol, sorbitol, PEG300, or PEG400, at a concentration of about 50 mM to about 1000 mM, such as about 100 mM to about 500 mM), or a charged tonicity modifier such as sodium chloride, sodium sulphate, sodium acetate, sodium lactate, glycine, histidine, or arginine, at a concentration of about 25 mM to about 500 mM such as about 50 mM to about 250 mM, and/or (iv) a preservative such as phenol, m-cresol, chlorocresol, benzyl alcohol, propylparaben, methylparaben, benzalkonium chloride, or benzethonium chloride, at a concentration of about 0.01 mM to about 100 mM.

In some embodiments, the conductivity of the aqueous solution is >2.5 mS/cm. In some embodiments, the conductivity of the aqueous solution is <2.5 mS/cm.

In some embodiments, the aqueous solution of the invention comprises,
(a) adalimumab at a concentration of about 10 mg/mL to about 250 mg/mL, about 25 mg/mL to about 75 mg/mL, about 80 mg/mL to about 125, about 130 mg/mL to about 180 mg/mL, or about 190 mg/mL to about 250 mg/mL, or about 50 mg/mL, about 100 mg/mL, about 150 mg/mL, about 160 mg/mL, about 200 mg/mL, or about 240 mg/mL; and
(b) a stabilizing amount of
(i) 1,2-propanediol or glycerol, or a mixture thereof, at a concentration of about 100 mM to about 500 mM (e.g. about 100 mM to about 300 mM, or about 100 mM to about 200 mM, e.g. about 100 mg/mL, about 130 mg/mL, or about 150 mg/mL),
(ii) arginine (e.g. L arginine) at a concentration of about 5 mM to about 150 mM, (e.g. about 50 mM to about 150 mM, such as about 50 mM, about 100 mM, about 60 mM to about 120 mM, 150 mM), and
(iii) methionine (e.g. L methionine) at a concentration of 2 mM to about 75 mM (e.g. 2 mM to about 50 mM, or about 10 mM to about 40 mM, or about 30 mM);
wherein the pH of the aqueous solution is between about pH 5.0 and about pH 6.5, e.g. about 5.2;
wherein the aqueous solution further comprises
(i) a buffer (e.g. histidine, succinate, maleate, acetate, phosphate, or TRIS) at a concentration of about 1 mM to about 20 mM about 2 mM to about 10 mM, e.g. about 8 mM,
(ii) a non-ionic surfactant (e.g. an alkyl glycoside, such as dodecyl maltoside, a polysorbate surfactant, such as polysorbate 80, or polysorbate 20, at a concentration of about 10 μg/mL to about 2000 μg/mL (e.g. about 50 μg/mL to about 1500 μg/mL, about 50 μg/mL to about 1250 μg/mL, about 50 μg/mL to about 1000 μg/mL, about 100 μg/mL to about 750 μg/mL, or about 100 μg/mL to about 500 μg/mL, or about 500 μg/mL, about 750 μg/mL, about 1000 μg/mL, about 1250 μg/mL, or about 1500 μg/mL),
optionally wherein the aqueous solution further comprises a tonicity modifier (e.g. sodium chloride or arginine), at a concentration of about 20 mM to about 250 mM (e.g. about 50 mM to about 250 mM, such as about 50 mM, about 60 mM, about 100 mM, or about 150 mM). In some embodiments, the conductivity of the aqueous solution is >2.5 mS/cm. In some embodiments, the conductivity of the aqueous solution is <2.5 mS/cm.

In some embodiments, the aqueous solution of the invention comprises,
(a) trastuzumab at a concentration of about 1 mg/mL to about 300 mg/mL (e.g. about 10 mg/mL to about 300 mg/mL, about 1 mg/mL to about 200 mg/mL, about 10 mg/mL to about 200 mg/mL, about 25 mg/mL to about 75 mg/mL, about 80 mg/mL to about 125, about 130 mg/mL to about 180 mg/mL, or about 190 mg/mL to about 250 mg/mL, or about 50 mg/mL, about 100 mg/mL, about 150 mg/mL, about 160 mg/mL, about 200 mg/mL, or about 240 mg/mL); and (b) a stabilizing amount of
   (i) 1,2-propanediol or glycerol, or a mixture thereof, at a concentration of about 100 mM to about 500 mM (e.g. about 150 mM to about 400 mM, about 150 mM to about 350 mM, or about 200 mM to about 300 mM, or about 200 mg/mL, about 250 mg/mL, or about 300 mg/mL),
   (ii) arginine (e.g. L arginine) at a concentration of about 5 mM to about 150 mM, (e.g. about 5 mM to about 100 mM, about 20 mM to about 125 mM, about 60 mM to about 120 mM, about 60 mM to about 100 mM, or about 20 mM to about 80 mM, or about 50 mM, about 60 mM, about 80 mM, about 100 mM, or about, 150 mM), and
   (iii) methionine (e.g. L methionine) at a concentration of 2 mM to about 75 mM (e.g. 2 mM to about 50 mM, or about 10 mM to about 40 mM, or about 30 mM);
   optionally, wherein the ratio (mM/mM) of arginine to methionine is between about 1:1 and about 10:1 (e.g. between about 2:1 and about 6:1), the ratio (mM/mM) of arginine to C3 polyol is between about 2:1 and 1:20 (e.g. between about 1:2 and about 1:10), the ratio (mM/mM) of methionine to C3 polyol is between about 1:1 and 1:40 (e.g. between about 1:4 and about 1:20), the ratio (mM/mM) of the combined concentration of arginine and methionine to C3 polyol is between about 4:1 and 1:20 (e.g. between about 2:1 and about 1:10), the ratio (wt/wt) of antibody protein to the combined weight of arginine and methionine is between about 1:15 and about 30:1 (e.g. between about 1:1 and about 25:1), or between about 1:2 and about 50:1 (e.g. between about 2:1 and about 25:1), and/or the ratio (wt/wt) of antibody protein to C3 polyol is between about 1:5 and about 200:1 (e.g. between about 2:1 and about 50:1) or between about 1:2 and about 200:1 (e.g. between about 2:1 and about 50:1); and
wherein the pH of the aqueous solution is between about pH 4.0 and about pH 8.0 (e.g. between about pH 5.0 and about pH 7.0 or between about pH 5.0 and about pH 6.5); optionally wherein the aqueous solution further comprises
   (i) a buffer (e.g. histidine, succinate, maleate, acetate, phosphate or TRIS) at a concentration of about 0.5 mM to about 50 mM (e.g. about 1 mM to about 20 mM, about 2 mM to about 10 mM, or about 2 mM to about 5 mM),
   (ii) a non-ionic surfactant (e.g. an alkyl glycoside, such as dodecyl maltoside, a polysorbate surfactant, such as polysorbate 80, or polysorbate 20, an alkyl ether of polyethylene glycol, such as polyethylene glycol (2) dodecyl ether, polyethylene glycol (2) oleyl ether or polyethylene glycol (2) hexadecyl ether, a block copolymer of polyethylene glycol and polypropylene glycol, such as poloxamer 188, poloxamer 407, poloxamer 171, or poloxamer 185, or an alkylphenyl ether of polyethylene glycol, such as 4-(1,1,3,3-tetramethyl-butyl) phenyl-polyethylene glycol, at a concentration of about 10 μg/mL to about 2000 μg/mL (e.g. about 50 μg/mL to about 1500 μg/mL, about 50 μg/mL to about 1250 μg/mL, about 50 μg/mL to about 1000 μg/mL, about 100 μg/mL to about 750 μg/mL, or about 100 μg/mL to about 500 μg/mL, or about 500 μg/mL, about 750 μg/mL, about 1000 μg/mL, about 1250 μg/mL, or about 1500 μg/mL),
   (iii) a tonicity modifier (e.g. an uncharged tonicity modifier, such as sucrose, trehalose, mannitol, sorbitol, PEG300, or PEG400, at a concentration of about 50 mM to about 1000 mM, such as about 100 mM to about 500 mM), or a charged tonicity modifier such as sodium chloride, sodium sulphate, sodium acetate, sodium lactate, glycine, histidine, or arginine, at a concentration of about 25 mM to about 500 mM such as about 50 mM to about 250 mM, and/or
   (iv) a preservative such as phenol, m-cresol, chlorocresol, benzyl alcohol, propylparaben, methylparaben, benzalkonium chloride, or benzethonium chloride, at a concentration of about 0.01 mM to about 100 mM.

In some embodiments, the conductivity of the aqueous solution is >2.5 mS/cm. In some embodiments, the conductivity of the aqueous solution is <2.5 mS/cm.

In some embodiments, the aqueous solution of the invention comprises,
(a) rituximab at a concentration of about 1 mg/mL to about 300 mg/mL (e.g. about 10 mg/mL to about 300 mg/mL, about 1 mg/mL to about 200 mg/mL, about 10 mg/mL to about 200 mg/mL, about 25 mg/mL to about 75 mg/mL, about 80 mg/mL to about 125, about 130 mg/mL to about 180 mg/mL, or about 190 mg/mL to about 250 mg/mL, or about 50 mg/mL, about 100 mg/mL, about 150 mg/mL, about 160 mg/mL, about 200 mg/mL, or about 240 mg/mL); and
(b) a stabilizing amount of
   (i) 1,2-propanediol or glycerol, or a mixture thereof, at a concentration of about 100 mM to about 500 mM (e.g. about 150 mM to about 400 mM, about 150 mM to about 350 mM, or about 200 mM to about 300 mM, or about 200 mg/mL, about 250 mg/mL, or about 300 mg/mL),
   (ii) arginine (e.g. L arginine) at a concentration of about 5 mM to about 150 mM, (e.g. about 5 mM to about 100 mM, about 20 mM to about 125 mM, about 60 mM to about 120 mM, about 60 mM or about 100 mM, or about 20 mM to about 80 mM, or about 50 mM, about 60 mM, about 80 mM, about 100 mM, or about 150 mM), and
   (iii) methionine (e.g. L methionine) at a concentration of 2 mM to about 75 mM (e.g. 2 mM to about 50 mM, or about 10 mM to about 40 mM, or about 30 mM);
   optionally, wherein the ratio (mM/mM) of arginine to methionine is between about 1:1 and about 10:1 (e.g. between about 2:1 and about 6:1), the ratio (mM/mM) of arginine to C3 polyol is between about 2:1 and 1:20 (e.g. between about 1:2 and about 1:10), the ratio (mM/mM) of methionine to C3 polyol is between about 1:1 and 1:40 (e.g. between about 1:4 and about 1:20), the ratio (mM/mM) of the combined concentration of arginine and methionine to C3 polyol is between about 4:1 and 1:20 (e.g. between about 2:1 and about 1:10), the ratio (wt/wt) of antibody protein to the combined weight of arginine and methionine is between about 1:15 and about 30:1 (e.g. between about 1:1 and about 25:1), or between about 1:2 and about 50:1 (e.g. between about 2:1 and about 25:1), and/or the ratio (wt/wt) of antibody protein to C3 polyol is between about 1:5 and about 200:1 (e.g. between about 2:1 and about 50:1) or between about 1:2 and about 200:1 (e.g. between about 2:1 and about 50:1); and
wherein the pH of the aqueous solution is between about pH 4.0 and about pH 8.0 (e.g. between about pH 5.0 and about pH 7.0 or between about pH 5.0 and about pH 6.5); optionally wherein the aqueous solution further comprises
   (i) a buffer (e.g. histidine, succinate, maleate, acetate, phosphate or TRIS) at a concentration of about 0.5 mM to about 50 mM (e.g. about 1 mM to about 20 mM, about 2 mM to about 10 mM, or about 2 mM to about 5 mM), (ii) a non-ionic surfactant (e.g. an alkyl glycoside, such as dodecyl maltoside, a polysorbate surfactant, such as polysorbate 80, or polysorbate 20, an alkyl ether of polyethylene glycol, such as polyethylene glycol (2) dodecyl ether, polyethylene glycol (2) oleyl ether or polyethylene glycol (2) hexadecyl ether, a block copolymer of polyethylene glycol and polypropylene glycol, such as poloxamer 188, poloxamer 407, poloxamer 171, or poloxamer 185, or an alkylphenyl ether of polyethylene glycol, such as 4-(1,1,3,3-tetramethylbutyl) phenyl-polyethylene glycol, at a concentration of about 10 µg/mL to about 2000 µg/mL (e.g. about 50 µg/mL to about 1500 µg/mL, about 50 µg/mL to about 1250 µg/mL, about 50 µg/mL to about 1000 µg/mL, about 100 µg/mL to about 750 µg/mL, or about 100 µg/mL to about 500 µg/mL, or about 500 µg/mL, about 750 µg/mL, about 1000 µg/mL, about 1250 µg/mL, or about 1500 µg/mL), (iii) a tonicity modifier (e.g. an uncharged tonicity modifier, such as sucrose, trehalose, mannitol, sorbitol, PEG300, or PEG400, at a concentration of about 50 mM to about 1000 mM, such as about 100 mM to about 500 mM), or a charged tonicity modifier such as sodium chloride, sodium sulphate, sodium acetate, sodium lactate, glycine, histidine, or arginine, at a concentration of about 25 mM to about 500 mM such as about 50 mM to about 250 mM, and/or (iv) a preservative such as phenol, m-cresol, chlorocresol, benzyl alcohol, propylparaben, methylparaben, benzalkonium chloride, or benzethonium chloride, at a concentration of about 0.01 mM to about 100 mM.

In some embodiments, the conductivity of the aqueous solution is >2.5 mS/cm. In some embodiments, the conductivity of the aqueous solution is <2.5 mS/cm.

In some embodiments, the aqueous solution of the invention comprises, (a) bevacizumab at a concentration of about 1 mg/mL to about 300 mg/mL (e.g. about 10 mg/mL to about 300 mg/mL, about 1 mg/mL to about 200 mg/mL, about 10 mg/mL to about 200 mg/mL, about 25 mg/mL to about 75 mg/mL, about 80 mg/mL to about 125, about 130 mg/mL to about 180 mg/mL, or about 190 mg/mL to about 250 mg/mL, or about 50 mg/mL, about 100 mg/mL, about 150 mg/mL, about 160 mg/mL, about 200 mg/mL, or about 240 mg/mL);

(b) a stabilizing amount of
(i) 1,2-propanediol or glycerol, or a mixture thereof, at a concentration of about 100 mM to about 500 mM (e.g. about 150 mM to about 400 mM, about 150 mM to about 350 mM, or about 200 mM to about 300 mM, or about 200 mg/mL, about 250 mg/mL, or about 300 mg/mL),
(ii) arginine (e.g. L arginine) at a concentration of about 5 mM to about 150 mM, (e.g. about 5 mM to about 100 mM, about 20 mM to about 125 mM, about 60 mM to about 120 mM, about 60 mM to about 100 mM, or about 20 mM to about 80 mM, or about 50 mM, about 60 mM, about 80 mM, about 100 mM, or about 150 mM), and
(iii) methionine (e.g. L methionine) at a concentration of 2 mM to about 75 mM (e.g. 2 mM to about 50 mM, or about 10 mM to about 40 mM, or about 30 mM);
optionally, wherein the ratio (mM/mM) of arginine to methionine is between about 1:1 and about 10:1 (e.g. between about 2:1 and about 6:1), the ratio (mM/mM) of arginine to C3 polyol is between about 2:1 and 1:20 (e.g. between about 1:2 and about 1:10), the ratio (mM/mM) of methionine to C3 polyol is between about 1:1 and 1:40 (e.g. between about 1:4 and about 1:20), the ratio (mM/mM) of the combined concentration of arginine and methionine to C3 polyol is between about 4:1 and 1:20 (e.g. between about 2:1 and about 1:10), the ratio (wt/wt) of antibody protein to the combined weight of arginine and methionine is between about 1:15 and about 30:1 (e.g. between about 1:1 and about 25:1), or between about 1:2 and about 50:1 (e.g. between about 2:1 and about 25:1), and/or the ratio (wt/wt) of antibody protein to C3 polyol is between about 1:5 and about 200:1 (e.g. between about 2:1 and about 50:1) or between about 1:2 and about 200:1 (e.g. between about 2:1 and about 50:1); and wherein the pH of the aqueous solution is between about pH 4.0 and about pH 8.0 (e.g. between about pH 5.0 and about pH 7.0 or between about pH 5.0 and about pH 6.5);

optionally wherein the aqueous solution further comprises
(i) a buffer (e.g. histidine, succinate, maleate, acetate, phosphate or TRIS) at a concentration of about 0.5 mM to about 50 mM (e.g. about 1 mM to about 20 mM, about 2 mM to about 10 mM, or about 2 mM to about 5 mM),
(ii) a non-ionic surfactant (e.g. an alkyl glycoside, such as dodecyl maltoside, a polysorbate surfactant, such as polysorbate 80, or polysorbate 20, an alkyl ether of polyethylene glycol, such as polyethylene glycol (2) dodecyl ether, polyethylene glycol (2) oleyl ether or polyethylene glycol (2) hexadecyl ether, a block copolymer of polyethylene glycol and polypropylene glycol, such as poloxamer 188, poloxamer 407, poloxamer 171, or poloxamer 185, or an alkylphenyl ether of polyethylene glycol, such as 4-(1,1,3,3-tetramethylbutyl) phenyl-polyethylene glycol, at a concentration of about 10 µg/mL to about 2000 µg/mL (e.g. about 50 µg/mL to about 1500 µg/mL, about 50 µg/mL to about 1250 µg/mL, about 50 µg/mL to about 1000 µg/mL, about 100 µg/mL to about 750 µg/mL, or about 100 µg/mL to about 500 µg/mL, or about 500 µg/mL, about 750 µg/mL, about 1000 µg/mL, about 1250 µg/mL, or about 1500 µg/mL),
(iii) a tonicity modifier (e.g. an uncharged tonicity modifier, such as sucrose, trehalose, mannitol, sorbitol, PEG300, or PEG400, at a concentration of about 50 mM to about 1000 mM, such as about 100 mM to about 500 mM), or a charged tonicity modifier such as sodium chloride, sodium sulphate, sodium acetate, sodium lactate, glycine, histidine, or arginine, at a concentration of about 25 mM to about 500 mM such as about 50 mM to about 250 mM, and/or
(iv) a preservative such as phenol, m-cresol, chlorocresol, benzyl alcohol, propylparaben, methylparaben, benzalkonium chloride, or benzethonium chloride, at a concentration of about 0.01 mM to about 100 mM.

In some embodiments, the conductivity of the aqueous solution is >2.5 mS/cm. In some embodiments, the conductivity of the aqueous solution is <2.5 mS/cm.

In some embodiments, the aqueous solution of the invention comprises, (a) bevacizumab at a concentration of about 1 mg/mL to about 300 mg/mL (e.g. about 10 mg/mL to about 300 mg/mL, about 1 mg/mL to about 200 mg/mL, about 10 mg/mL to about 200 mg/mL, about 25 mg/mL to about 75 mg/mL, about 80 mg/mL to about 125, about 130 mg/mL to about 180 mg/mL, or about 190 mg/mL to about 250 mg/mL, or about 50 mg/mL, about 100 mg/mL, about 150 mg/mL, about 160 mg/mL, about 200 mg/mL, or about 240 mg/mL); and (b) a stabilizing amount of
  (i) 1,2-propanediol or glycerol, or a mixture thereof, at a concentration of about 100 mM to about 500 mM (e.g. about 150 mM to about 400 mM, about 150 mM to about 350 mM, or about 200 mM to about 300 mM, or about 200 mg/mL, about 250 mg/mL, or about 300 mg/mL),
  (ii) arginine (e.g. L arginine) at a concentration of about 5 mM to about 150 mM, (e.g. about 5 mM to about 100 mM, about 20 mM to about 125 mM, about 60 mM to about 120 mM, about 60 mM to about 100 mM, or about 20 mM to about 80 mM, or about 50 mM, about 60 mM, about 80 mM, about 100 mM, or about 150 mM), and
  (iii) methionine (e.g. L methionine) at a concentration of 2 mM to about 75 mM (e.g. 2 mM to about 50 mM, or about 10 mM to about 40 mM, or about 30 mM);
optionally, wherein the ratio (mM/mM) of arginine to methionine is between about 1:1 and about 10:1 (e.g. between about 2:1 and about 6:1), the ratio (mM/mM) of arginine to C3 polyol is between about 2:1 and 1:20 (e.g. between about 1:2 and about 1:10), the ratio (mM/mM) of methionine to C3 polyol is between about 1:1 and 1:40 (e.g. between about 1:4 and about 1:20), the ratio (mM/mM) of the combined concentration of arginine and methionine to C3 polyol is between about 4:1 and 1:20 (e.g. between about 2:1 and about 1:10), the ratio (wt/wt) of antibody protein to the combined weight of arginine and methionine is between about 1:15 and about 30:1 (e.g. between about 1:1 and about 25:1), or between about 1:2 and about 50:1 (e.g. between about 2:1 and about 25:1), and/or the ratio (wt/wt) of antibody protein to C3 polyol is between about 1:5 and about 200:1 (e.g. between about 2:1 and about 50:1) or between about 1:2 and about 200:1 (e.g. between about 2:1 and about 50:1); and
wherein the pH of the aqueous solution is between about pH 4.0 and about pH 8.0 (e.g. between about pH 5.0 and about pH 7.0 or between about pH 5.0 and about pH 6.5); optionally wherein the aqueous solution further comprises
  (i) a buffer (e.g. histidine, succinate, maleate, acetate, phosphate or TRIS) at a concentration of about 0.5 mM to about 50 mM (e.g. about 1 mM to about 20 mM, about 2 mM to about 10 mM, or about 2 mM to about 5 mM),
  (ii) a non-ionic surfactant (e.g. an alkyl glycoside, such as dodecyl maltoside, a polysorbate surfactant, such as polysorbate 80, or polysorbate 20, an alkyl ether of polyethylene glycol, such as polyethylene glycol (2) dodecyl ether, polyethylene glycol (2) oleyl ether or polyethylene glycol (2) hexadecyl ether, a block copolymer of polyethylene glycol and polypropylene glycol, such as poloxamer 188, poloxamer 407, poloxamer 171, or poloxamer 185, or an alkylphenyl ether of polyethylene glycol, such as 4-(1,1,3,3-tetramethylbutyl) phenyl-polyethylene glycol, at a concentration of about 10 μg/mL to about 2000 μg/mL (e.g. about 50 μg/mL to about 1500 μg/mL, about 50 μg/mL to about 1250 μg/mL, about 50 μg/mL to about 1000 μg/mL, about 100 μg/mL to about 750 μg/mL, or about 100 μg/mL to about 500 μg/mL, or about 500 μg/mL, about 750 μg/mL, about 1000 μg/mL, about 1250 μg/mL, or about 1500 μg/mL),
  (iii) a tonicity modifier (e.g. an uncharged tonicity modifier, such as sucrose, trehalose, mannitol, sorbitol, PEG300, or PEG400, at a concentration of about 50 mM to about 1000 mM, such as about 100 mM to about 500 mM), or a charged tonicity modifier such as sodium chloride, sodium sulphate, sodium acetate, sodium lactate, glycine, histidine, or arginine, at a concentration of about 25 mM to about 500 mM such as about 50 mM to about 250 mM, and/or
  (iv) a preservative such as phenol, m-cresol, chlorocresol, benzyl alcohol, propylparaben, methylparaben, benzalkonium chloride, or benzethonium chloride, at a concentration of about 0.01 mM to about 100 mM.

In some embodiments, the conductivity of the aqueous solution is >2.5 mS/cm. In some embodiments, the conductivity of the aqueous solution is <2.5 mS/cm.

In some embodiments, the aqueous solution of the invention comprises,
(a) cetuximab at a concentration of about 1 mg/mL to about 300 mg/mL (e.g. about 10 mg/mL to about 300 mg/mL, about 1 mg/mL to about 200 mg/mL, about 10 mg/mL to about 200 mg/mL, about 25 mg/mL to about 75 mg/mL, about 80 mg/mL to about 125, about 130 mg/mL to about 180 mg/mL, or about 190 mg/mL to about 250 mg/mL, or about 50 mg/mL, about 100 mg/mL, about 150 mg/mL, about 160 mg/mL, about 200 mg/mL, or about 240 mg/mL); and
(b) a stabilizing amount of
  (i) 1,2-propanediol or glycerol, or a mixture thereof, at a concentration of about 100 mM to about 500 mM (e.g. about 150 mM to about 400 mM, about 150 mM to about 350 mM, or about 200 mM to about 300 mM, or about 200 mg/mL, about 250 mg/mL, or about 300 mg/mL),
  (ii) arginine (e.g. L arginine) at a concentration of about 5 mM to about 150 mM, (e.g. about 5 mM to about 100 mM, about 20 mM to about 125 mM, about 60 mM to about 120 mM, about 60 mM to about 100 mM, or about 20 mM to about 80 mM, or about 50 mM, about 60 mM, about 80 mM, about 100 mM, or about 150 mM), and
  (iii) methionine (e.g. L methionine) at a concentration of 2 mM to about 75 mM (e.g. 2 mM to about 50 mM, or about 10 mM to about 40 mM, or about 30 mM);
optionally, wherein the ratio (mM/mM) of arginine to methionine is between about 1:1 and about 10:1 (e.g. between about 2:1 and about 6:1), the ratio (mM/mM) of arginine to C3 polyol is between about 2:1 and 1:20 (e.g. between about 1:2 and about 1:10), the ratio (mM/mM) of methionine to C3 polyol is between about 1:1 and 1:40 (e.g. between about 1:4 and about 1:20), the ratio (mM/mM) of the combined concentration of arginine and methionine to C3 polyol is between about 4:1 and 1:20 (e.g. between about 2:1 and about 1:10), the ratio (wt/wt) of antibody protein to the combined weight of arginine and methionine is between about 1:15 and about 30:1 (e.g. between about 1:1 and about 25:1), or between about 1:2 and about 50:1 (e.g. between about 2:1 and about 25:1), and/or the ratio (wt/wt) of antibody protein to C3 polyol is between about 1:5 and about 200:1 (e.g. between about 2:1 and about 50:1) or between about 1:2 and about 200:1 (e.g. between about 2:1 and about 50:1); and
wherein the pH of the aqueous solution is between about pH 4.0 and about pH 8.0 (e.g. between about pH 5.0 and about pH 7.0 or between about pH 5.0 and about pH 6.5); optionally wherein the aqueous solution further comprises
  (i) a buffer (e.g. histidine, succinate, maleate, acetate, phosphate or TRIS) at a concentration of about 0.5 mM to about 50 mM (e.g. about 1 mM to about 20 mM, about 2 mM to about 10 mM, or about 2 mM to about 5 mM), (ii) a non-ionic surfactant (e.g. an alkyl glycoside, such as dodecyl maltoside, a polysorbate surfactant, such as polysorbate 80, or polysorbate 20, an alkyl ether of polyethylene glycol, such as polyethylene glycol (2) dodecyl ether, polyethylene glycol (2) oleyl ether or polyethylene glycol (2) hexadecyl ether, a block copolymer of polyethylene glycol and polypropylene glycol, such as poloxamer 188, poloxamer 407, poloxamer 171, or poloxamer 185, or an alkylphenyl ether of polyethylene glycol, such as 4-(1,1,3,3-tetramethylbutyl) phenyl-polyethylene glycol, at a concentration of about 10 μg/mL to about 2000 μg/mL (e.g. about 50 μg/mL to about 1500 μg/mL, about 50 μg/mL to about 1250 μg/mL, about 50 μg/mL to about 1000 μg/mL, about 100 μg/mL to about 750 μg/mL, or about 100 μg/mL to about 500 μg/mL, or about 500 μg/mL, about 750 μg/mL, about 1000 μg/mL, about 1250 μg/mL, or about 1500 μg/mL), (iii) a tonicity modifier (e.g. an uncharged tonicity modifier, such as sucrose, trehalose, mannitol, sorbitol, PEG300, or PEG400, at a concentration of about 50 mM to about 1000 mM, such as about 100 mM to about 500 mM), or a charged tonicity modifier such as sodium chloride, sodium sulphate, sodium acetate, sodium lactate, glycine, histidine, or arginine, at a concentration of about 25 mM to about 500 mM such as about 50 mM to about 250 mM, and/or (v) a preservative such as phenol, m-cresol, chlorocresol, benzyl alcohol, propylparaben, methylparaben, benzalkonium chloride, or benzethonium chloride, at a concentration of about 0.01 mM to about 100 mM.

In some embodiments, the conductivity of the aqueous solution is >2.5 mS/cm. In some embodiments, the conductivity of the aqueous solution is <2.5 mS/cm.

In some embodiments, the aqueous solution of the invention comprises, (a) ipilimumab at a concentration of about 1 mg/mL to about 300 mg/mL (e.g. about 10 mg/mL to about 300 mg/mL, about 1 mg/mL to about 200 mg/mL, about 10 mg/mL to about 200 mg/mL, about 25 mg/mL to about 75 mg/mL, about 80 mg/mL to about 125, about 130 mg/mL to about 180 mg/mL, or about 190 mg/mL to about 250 mg/mL, or about 50 mg/mL, about 100 mg/mL, about 150 mg/mL, about 160 mg/mL, about 200 mg/mL, or about 240 mg/mL);

(b) a stabilizing amount of
  (i) 1,2-propanediol or glycerol, or a mixture thereof, at a concentration of about 100 mM to about 500 mM (e.g. about 150 mM to about 400 mM, about 150 mM to about 350 mM, or about 200 mM to about 300 mM, or about 200 mg/mL, about 250 mg/mL, or about 300 mg/mL), (a) arginine (e.g. L arginine) at a concentration of about 5 mM to about 150 mM, (e.g. about 5 mM to about 100 mM, about 20 mM to about 125 mM, about 60 mM to about 120 mM, about 60 mM to about 100 mM, or about 20 mM to about 80 mM, or about 50 mM, about 60 mM, about 80 mM, about 100 mM, or about, about 10 mg/mL to about 300 mg/mL, about 1 mg/mL to about 200 mg/mL, about 10 mg/mL to about 200 mg/mL, about 25 mg/mL to about 75 mg/mL, about 80 mg/mL to about 125, or about 130 mg/mL to about 180 mg/mL, or about 190 mg/mL to about 250 mg/mL, or about 50 mg/mL, about 100 mg/mL, about 150 mg/mL, or about 200 mg/mL); and (b) a stabilizing amount of
  (i) 1,2-propanediol or glycerol, or a mixture thereof at a concentration of about 100 mM to about 500 mM (e.g. about 150 mM to about 400 mM, about 150 mM to 350 mM, or about 200 mM to about 300 mM, or about 200 mg/mL, about 250 mg/mL, or about 300 mg/mL), and (ii) methionine (e.g. L methionine) at a concentration of 2 mM to about 75 mM (e.g. 2 mM to about 50 mM, or about 10 mM to about 40 mM, or about 30 mM);

optionally, wherein the ratio (mM/mM) of arginine to methionine is between about 1:1 and about 10:1 (e.g. between about 2:1 and about 6:1), the ratio (mM/mM) of arginine to C3 polyol is between about 2:1 and 1:20 (e.g. between about 1:2 and about 1:10), the ratio (mM/mM) of methionine to C3 polyol is between about 1:1 and 1:40 (e.g. between about 1:4 and about 1:20), the ratio (mM/mM) of the combined concentration of arginine and methionine to C3 polyol is between about 4:1 and 1:20 (e.g. between about 2:1 and about 1:10), the ratio (wt/wt) of antibody protein to the combined weight of arginine and methionine is between about 1:15 and about 30:1 (e.g. between about 1:1 and about 25:1), or between about 1:2 and about 50:1 (e.g. between about 2:1 and about 25:1), and/or the ratio (wt/wt) of antibody protein to C3 polyol is between about 1:5 and about 200:1 (e.g. between about 2:1 and about 50:1) or between about 1:2 and about 200:1 (e.g. between about 2:1 and about 50:1); and wherein the pH of the aqueous solution is between about pH 4.0 and about pH 8.0 (e.g. between about pH 5.0 and about pH 7.0 or between about pH 5.0 and about pH 6.5);

optionally wherein the aqueous solution further comprises
  (i) a buffer (e.g. histidine, succinate, maleate, acetate, phosphate or TRIS) at a concentration of about 0.5 mM to about 50 mM (e.g. about 1 mM to about 20 mM, about 2 mM to about 10 mM, or about 2 mM to about 5 mM), (ii) a non-ionic surfactant (e.g. an alkyl glycoside, such as dodecyl maltoside, a polysorbate surfactant, such as polysorbate 80, or polysorbate 20, an alkyl ether of polyethylene glycol, such as polyethylene glycol (2) dodecyl ether, polyethylene glycol (2) oleyl ether or polyethylene glycol (2) hexadecyl ether, a block copolymer of polyethylene glycol and polypropylene glycol, such as poloxamer 188, poloxamer 407, poloxamer 171, or poloxamer 185, or an alkylphenyl ether of polyethylene glycol, such as 4-(1,1,3,3-tetramethylbutyl) phenyl-polyethylene glycol, at a concentration of about 10 μg/mL to about 2000 μg/mL (e.g. about 50 μg/mL to about 1500 μg/mL, about 50 μg/mL to about 1250 μg/mL, about 50 μg/mL to about 1000 μg/mL, about 100 μg/mL to about 750 μg/mL, or about 100 μg/mL to about 500 μg/mL, or about 500 μg/mL, about 750 μg/mL, about 1000 μg/mL, about 1250 μg/mL, or about 1500 μg/mL), (iii) a tonicity modifier (e.g. an uncharged tonicity modifier, such as sucrose, trehalose, mannitol, sorbitol, PEG300, or PEG400, at a concentration of about 50 mM to about 1000 mM, such as about 100 mM to about 500 mM), or a charged tonicity modifier such as sodium chloride, sodium sulphate, sodium acetate, sodium lactate, glycine, histidine, or arginine, at a concentration of about 25 mM to about 500 mM such as about 50 mM to about 250 mM, and/or (vi) a preservative such as phenol, m-cresol, chlorocresol, benzyl alcohol, propylparaben, methylparaben, benzalkonium chloride, or benzethonium chloride, at a concentration of about 0.01 mM to about 100 mM.

In some embodiments, the conductivity of the aqueous solution is >2.5 mS/cm. In some embodiments, the conductivity of the aqueous solution is <2.5 mS/cm.

In some embodiments, the aqueous solution of the invention comprises, (c) infliximab at a concentration of about 1 mg/mL to about 300 mg/mL (e.g. about 10 mg/mL to about 300 mg/mL, about 1 mg/mL to about 200 mg/mL, about 10 mg/mL to about 200 mg/mL, about 25 mg/mL to about 75 mg/mL, about 80 mg/mL to about 125, about 130 mg/mL to about 180 mg/mL, or about 190 mg/mL to about 250 mg/mL, or about 50 mg/mL, about 100 mg/mL, about 150 mg/mL, about 160 mg/mL, about 200 mg/mL, or about 240 mg/mL); and (d) a stabilizing amount of
  (i) 1,2-propanediol or glycerol, or a mixture thereof, at a concentration of about 100 mM to about 500 mM (e.g. about 150 mM to about 400 mM, about 150 mM to about 350 mM, or about 200 mM to about 300 mM, or about 200 mg/mL, about 250 mg/mL, or about 300 mg/mL),
  (ii) arginine (e.g. L arginine) at a concentration of about 5 mM to about 150 mM, (e.g. about 5 mM to about 100 mM, about 20 mM to about 125 mM, about 60 mM to about 120 mM, about 60 mM to about 100 mM, or about 20 mM to about 80 mM, or about 50 mM, about 60 mM, about 80 mM, about 100 mM, or about 150 mM), and
  (iii) methionine (e.g. L methionine) at a concentration of 2 mM to about 75 mM (e.g. 2 mM to about 50 mM, or about 10 mM to about 40 mM, or about 30 mM);
  optionally, wherein the ratio (mM/mM) of arginine to methionine is between about 1:1 and about 10:1 (e.g. between about 2:1 and about 6:1), the ratio (mM/mM) of arginine to C3 polyol is between about 2:1 and 1:20 (e.g. between about 1:2 and about 1:10), the ratio (mM/mM) of methionine to C3 polyol is between about 1:1 and 1:40 (e.g. between about 1:4 and about 1:20), the ratio (mM/mM) of the combined concentration of arginine and methionine to C3 polyol is between about 4:1 and 1:20 (e.g. between about 2:1 and about 1:10), the ratio (wt/wt) of antibody protein to the combined weight of arginine and methionine is between about 1:15 and about 30:1 (e.g. between about 1:1 and about 25:1), or between about 1:2 and about 50:1 (e.g. between about 2:1 and about 25:1), and/or the ratio (wt/wt) of antibody protein to C3 polyol is between about 1:5 and about 200:1 (e.g. between about 2:1 and about 50:1) or between about 1:2 and about 200:1 (e.g. between about 2:1 and about 50:1); and wherein the pH of the aqueous solution is between about pH 4.0 and about pH 8.0 (e.g. between about pH 5.0 and about pH 7.0 or between about pH 5.0 and about pH 6.5); optionally wherein the aqueous solution further comprises
  (i) a buffer (e.g. histidine, succinate, maleate, acetate, phosphate or TRIS) at a concentration of about 0.5 mM to about 50 mM (e.g. about 1 mM to about 20 mM, about 2 mM to about 10 mM, or about 2 mM to about 5 mM),
  (ii) a non-ionic surfactant (e.g. an alkyl glycoside, such as dodecyl maltoside, a polysorbate surfactant, such as polysorbate 80, or polysorbate 20, an alkyl ether of polyethylene glycol, such as polyethylene glycol (2) dodecyl ether, polyethylene glycol (2) oleyl ether or polyethylene glycol (2) hexadecyl ether, a block copolymer of polyethylene glycol and polypropylene glycol, such as poloxamer 188, poloxamer 407, poloxamer 171, or poloxamer 185, or an alkylphenyl ether of polyethylene glycol, such as 4-(1,1,3,3-tetramethylbutyl) phenyl-polyethylene glycol, at a concentration of about 10 µg/mL to about 2000 µg/mL (e.g. about 50 µg/mL to about 1500 µg/mL, about 50 µg/mL to about 1250 µg/mL, about 50 µg/mL to about 1000 µg/mL, about 100 µg/mL to about 750 µg/mL, or about 100 µg/mL to about 500 µg/mL, or about 500 µg/mL, about 750 µg/mL, about 1000 µg/mL, about 1250 µg/mL, or about 1500 µg/mL),
  (iii) a tonicity modifier (e.g. an uncharged tonicity modifier, such as sucrose, trehalose, mannitol, sorbitol, PEG300, or PEG400, at a concentration of about 50 mM to about 1000 mM, such as about 100 mM to about 500 mM), or a charged tonicity modifier such as sodium chloride, sodium sulphate, sodium acetate, sodium lactate, glycine, histidine, or arginine, at a concentration of about 25 mM to about 500 mM such as about 50 mM to about 250 mM, and/or
  (vii) a preservative such as phenol, m-cresol, chlorocresol, benzyl alcohol, propylparaben, methylparaben, benzalkonium chloride, or benzethonium chloride, at a concentration of about 0.01 mM to about 100 mM.

In some embodiments, the conductivity of the aqueous solution is >2.5 mS/cm. In some embodiments, the conductivity of the aqueous solution is <2.5 mS/cm.

In some embodiments, the aqueous solution of the invention comprises, (a) ranibizumab at a concentration of about 1 mg/mL to about 300 mg/mL (e.g. about 10 mg/mL to about 300 mg/mL, about 1 mg/mL to about 200 mg/mL, about 10 mg/mL to about 200 mg/mL, about 25 mg/mL to about 75 mg/mL, about 80 mg/mL to about 125, about 130 mg/mL to about 180 mg/mL, or about 190 mg/mL to about 250 mg/mL, or about 50 mg/mL, about 100 mg/mL, about 150 mg/mL, about 160 mg/mL, about 200 mg/mL, or about 240 mg/mL); and (b) a stabilizing amount of
  (i) 1,2-propanediol or glycerol, or a mixture thereof, at a concentration of about 100 mM to about 500 mM (e.g. about 150 mM to about 400 mM, about 150 mM to about 350 mM, or about 200 mM to about 300 mM, or about 200 mg/mL, about 250 mg/mL, or about 300 mg/mL),
  (ii) arginine (e.g. L arginine) at a concentration of about 5 mM to about 150 mM, (e.g. about 5 mM to about 100 mM, about 20 mM to about 125 mM, about 60 mM to about 120 mM, about 60 mM to about 100 mM, or about 20 mM to about 80 mM, or about 50 mM, about 60 mM, about 80 mM, about 100 mM, or about 150 mM), and
  (iii) methionine (e.g. L methionine) at a concentration of 2 mM to about 75 mM (e.g. 2 mM to about 50 mM, or about 10 mM to about 40 mM, or about 30 mM);
  optionally, wherein the ratio (mM/mM) of arginine to methionine is between about 1:1 and about 10:1 (e.g. between about 2:1 and about 6:1), the ratio (mM/mM) of arginine to C3 polyol is between about 2:1 and 1:20 (e.g. between about 1:2 and about 1:10), the ratio (mM/mM) of methionine to C3 polyol is between about 1:1 and 1:40 (e.g. between about 1:4 and about 1:20), the ratio (mM/mM) of the combined concentration of arginine and methionine to C3 polyol is between about 4:1 and 1:20 (e.g. between about 2:1 and about 1:10), the ratio (wt/wt) of antibody protein to the combined weight of arginine and methionine is between about 1:15 and about 30:1 (e.g. between about 1:1 and about 25:1), or between about 1:2 and about 50:1 (e.g. between about 2:1 and about 25:1), and/or the ratio (wt/wt) of antibody protein to C3 polyol is between about 1:5 and about 200:1 (e.g. between about 2:1 and about 50:1) or between about 1:2 and about 200:1 (e.g. between about 2:1 and about 50:1); and wherein the pH of the aqueous solution is between about pH 4.0 and about pH 8.0 (e.g. between about pH 5.0 and about pH 7.0 or between about pH 5.0 and about pH 6.5);

optionally wherein the aqueous solution further comprises (i) a buffer (e.g. histidine, succinate, maleate, acetate, phosphate or TRIS) at a concentration of about 0.5 mM to about 50 mM (e.g. about 1 mM to about 20 mM, about 2 mM to about 10 mM, or about 2 mM to about 5 mM), (ii) a non-ionic surfactant (e.g. an alkyl glycoside, such as dodecyl maltoside, a polysorbate surfactant, such as polysorbate 80, or polysorbate 20, an alkyl ether of polyethylene glycol, such as polyethylene glycol (2) dodecyl ether, polyethylene glycol (2) oleyl ether or polyethylene glycol (2) hexadecyl ether, a block copolymer of polyethylene glycol and polypropylene glycol, such as poloxamer 188, poloxamer 407, poloxamer 171, or poloxamer 185, or an alkylphenyl ether of polyethylene glycol, such as 4-(1,1,3,3-tetramethylbutyl) phenyl-polyethylene glycol, at a concentration of about 10 μg/mL to about 2000 μg/mL (e.g. about 50 μg/mL to about 1500 μg/mL, about 50 μg/mL to about 1250 μg/mL, about 50 μg/mL to about 1000 μg/mL, about 100 μg/mL to about 750 μg/mL, or about 100 μg/mL to about 500 μg/mL, or about 500 μg/mL, about 750 μg/mL, about 1000 μg/mL, about 1250 μg/mL, or about 1500 μg/mL), (iii) a tonicity modifier (e.g. an uncharged tonicity modifier, such as sucrose, trehalose, mannitol, sorbitol, PEG300, or PEG400, at a concentration of about 50 mM to about 1000 mM, such as about 100 mM to about 500 mM), or a charged tonicity modifier such as sodium chloride, sodium sulphate, sodium acetate, sodium lactate, glycine, histidine, or arginine, at a concentration of about 25 mM to about 500 mM such as about 50 mM to about 250 mM, and/or (iv) a preservative such as phenol, m-cresol, chlorocresol, benzyl alcohol, propylparaben, methylparaben, benzalkonium chloride, or benzethonium chloride, at a concentration of about 0.01 mM to about 100 mM.

In some embodiments, the conductivity of the aqueous solution is >2.5 mS/cm. In some embodiments, the conductivity of the aqueous solution is <2.5 mS/cm.

In some embodiments, the aqueous solution of the invention comprises, (a) pembrolizumab at a concentration of about 1 mg/mL to about 300 mg/mL (e.g. about 10 mg/mL to about 300 mg/mL, about 1 mg/mL to about 200 mg/mL, about 10 mg/mL to about 200 mg/mL, about 25 mg/mL to about 75 mg/mL, about 80 mg/mL to about 125, about 130 mg/mL to about 180 mg/mL, or about 190 mg/mL to about 250 mg/mL, or about 50 mg/mL, about 100 mg/mL, about 150 mg/mL, about 160 mg/mL, about 200 mg/mL, or about 240 mg/mL); and (b) a stabilizing amount of (i) 1,2-propanediol or glycerol, or a mixture thereof, at a concentration of about 100 mM to about 500 mM (e.g. about 150 mM to about 400 mM, about 150 mM to about 350 mM, or about 200 mM to about 300 mM, or about 200 mg/mL, about 250 mg/mL, or about 300 mg/mL), (ii) arginine (e.g. L arginine) at a concentration of about 5 mM to about 150 mM, (e.g. about 5 mM to about 100 mM, about 20 mM to about 125 mM, about 60 mM to about 120 mM, about 60 mM to about 100 mM, or about 20 mM to about 80 mM, or about 50 mM, about 60 mM, about 80 mM, about 100 mM, or about 150 mM), and (iii) methionine (e.g. L methionine) at a concentration of 2 mM to about 75 mM (e.g. 2 mM to about 50 mM, or about 10 mM to about 40 mM, or about 30 mM);

optionally, wherein the ratio (mM/mM) of arginine to methionine is between about 1:1 and about 10:1 (e.g. between about 2:1 and about 6:1), the ratio (mM/mM) of arginine to C3 polyol is between about 2:1 and 1:20 (e.g. between about 1:2 and about 1:10), the ratio (mM/mM) of methionine to C3 polyol is between about 1:1 and 1:40 (e.g. between about 1:4 and about 1:20), the ratio (mM/mM) of the combined concentration of arginine and methionine to C3 polyol is between about 4:1 and 1:20 (e.g. between about 2:1 and about 1:10), the ratio (wt/wt) of antibody protein to the combined weight of arginine and methionine is between about 1:15 and about 30:1 (e.g. between about 1:1 and about 25:1), or between about 1:2 and about 50:1 (e.g. between about 2:1 and about 25:1), and/or the ratio (wt/wt) of antibody protein to C3 polyol is between about 1:5 and about 200:1 (e.g. between about 2:1 and about 50:1) or between about 1:2 and about 200:1 (e.g. between about 2:1 and about 50:1); and wherein the pH of the aqueous solution is between about pH 4.0 and about pH 8.0 (e.g. between about pH 5.0 and about pH 7.0 or between about pH 5.0 and about pH 6.5);

optionally wherein the aqueous solution further comprises (i) a buffer (e.g. histidine, succinate, maleate, acetate, phosphate or TRIS) at a concentration of about 0.5 mM to about 50 mM (e.g. about 1 mM to about 20 mM, about 2 mM to about 10 mM, or about 2 mM to about 5 mM), (ii) a non-ionic surfactant (e.g. an alkyl glycoside, such as dodecyl maltoside, a polysorbate surfactant, such as polysorbate 80, or polysorbate 20, an alkyl ether of polyethylene glycol, such as polyethylene glycol (2) dodecyl ether, polyethylene glycol (2) oleyl ether or polyethylene glycol (2) hexadecyl ether, a block copolymer of polyethylene glycol and polypropylene glycol, such as poloxamer 188, poloxamer 407, poloxamer 171, or poloxamer 185, or an alkylphenyl ether of polyethylene glycol, such as 4-(1,1,3,3-tetramethylbutyl) phenyl-polyethylene glycol, at a concentration of about 10 μg/mL to about 2000 μg/mL (e.g. about 50 μg/mL to about 1500 μg/mL, about 50 μg/mL to about 1250 μg/mL, about 50 μg/mL to about 1000 μg/mL, about 100 μg/mL to about 750 μg/mL, or about 100 μg/mL to about 500 μg/mL, or about 500 μg/mL, about 750 μg/mL, about 1000 μg/mL, about 1250 μg/mL, or about 1500 μg/mL), (iii) a tonicity modifier (e.g. an uncharged tonicity modifier, such as sucrose, trehalose, mannitol, sorbitol, PEG300, or PEG400, at a concentration of about 50 mM to about 1000 mM, such as about 100 mM to about 500 mM), or a charged tonicity modifier such as sodium chloride, sodium sulphate, sodium acetate, sodium lactate, glycine, histidine, or arginine, at a concentration of about 25 mM to about 500 mM such as about 50 mM to about 250 mM, and/or (iv) a preservative such as phenol, m-cresol, chlorocresol, benzyl alcohol, propylparaben, methylparaben, benzalkonium chloride, or benzethonium chloride, at a concentration of about 0.01 mM to about 100 mM.

In some embodiments, the conductivity of the aqueous solution is >2.5 mS/cm. In some embodiments, the conductivity of the aqueous solution is <2.5 mS/cm.

In some embodiments, the aqueous solution of the invention comprises,
(a) nevolimumab at a concentration of about 1 mg/mL to about 300 mg/mL (e.g. about 10 mg/mL to about 300 mg/mL, about 1 mg/mL to about 200 mg/mL, about 10 mg/mL to about 200 mg/mL, about 25 mg/mL to about 75 mg/mL, about 80 mg/mL to about 125, about 130 mg/mL to about 180 mg/mL, or about 190 mg/mL to about 250 mg/mL, or about 50 mg/mL, about 100 mg/mL, about 150 mg/mL, about 160 mg/mL, about 200 mg/mL, or about 240 mg/mL);
(b) a stabilizing amount of
  (i) 1,2-propanediol or glycerol, or a mixture thereof, at a concentration of about 100 mM to about 500 mM (e.g. about 150 mM to about 400 mM, about 150 mM to about 350 mM, or about 200 mM to about 300 mM, or about 200 mg/mL, about 250 mg/mL, or about 300 mg/mL),
  (ii) arginine (e.g. L arginine) at a concentration of about 5 mM to about 150 mM, (e.g. about 5 mM to about 100 mM, about 20 mM to about 125 mM, about 60 mM to about 120 mM, about 60 mM to about 100 mM, or about 20 mM to about 80 mM, or about 50 mM, about 60 mM, about 80 mM, about 100 mM, or about 150 mM), and
  (iii) methionine (e.g. L methionine) at a concentration of 2 mM to about 75 mM (e.g. 2 mM to about 50 mM, or about 10 mM to about 40 mM, or about 30 mM);
  optionally, wherein the ratio (mM/mM) of arginine to methionine is between about 1:1 and about 10:1 (e.g. between about 2:1 and about 6:1), the ratio (mM/mM) of arginine to C3 polyol is between about 2:1 and 1:20 (e.g. between about 1:2 and about 1:10), the ratio (mM/mM) of methionine to C3 polyol is between about 1:1 and 1:40 (e.g. between about 1:4 and about 1:20), the ratio (mM/mM) of the combined concentration of arginine and methionine to C3 polyol is between about 4:1 and 1:20 (e.g. between about 2:1 and about 1:10), the ratio (wt/wt) of antibody protein to the combined weight of arginine and methionine is between about 1:15 and about 30:1 (e.g. between about 1:1 and about 25:1), or between about 1:2 and about 50:1 (e.g. between about 2:1 and about 25:1), and/or the ratio (wt/wt) of antibody protein to C3 polyol is between about 1:5 and about 200:1 (e.g. between about 2:1 and about 50:1) or between about 1:2 and about 200:1 (e.g. between about 2:1 and about 50:1); and
wherein the pH of the aqueous solution is between about pH 4.0 and about pH 8.0 (e.g. between about pH 5.0 and about pH 7.0 or between about pH 5.0 and about pH 6.5);
optionally wherein the aqueous solution further comprises
  (i) a buffer (e.g. histidine, succinate, maleate, acetate, phosphate or TRIS) at a concentration of about 0.5 mM to about 50 mM (e.g. about 1 mM to about 20 mM, about 2 mM to about 10 mM, or about 2 mM to about 5 mM),
  (ii) a non-ionic surfactant (e.g. an alkyl glycoside, such as dodecyl maltoside, a polysorbate surfactant, such as polysorbate 80, or polysorbate 20, an alkyl ether of polyethylene glycol, such as polyethylene glycol (2) dodecyl ether, polyethylene glycol (2) oleyl ether or polyethylene glycol (2) hexadecyl ether, a block copolymer of polyethylene glycol and polypropylene glycol, such as poloxamer 188, poloxamer 407, poloxamer 171, or poloxamer 185, or an alkylphenyl ether of polyethylene glycol, such as 4-(1,1,3,3-tetramethyl-butyl) phenyl-polyethylene glycol, at a concentration of about 10 μg/mL to about 2000 μg/mL (e.g. about 50 μg/mL to about 1500 μg/mL, about 50 μg/mL to about 1250 μg/mL, about 50 μg/mL to about 1000 μg/mL, about 100 μg/mL to about 750 μg/mL, or about 100 μg/mL to about 500 μg/mL, or about 500 μg/mL, about 750 μg/mL, about 1000 μg/mL, about 1250 μg/mL, or about 1500 μg/mL),
  (iii) a tonicity modifier (e.g. an uncharged tonicity modifier, such as sucrose, trehalose, mannitol, sorbitol, PEG300, or PEG400, at a concentration of about 50 mM to about 1000 mM, such as about 100 mM to about 500 mM), or a charged tonicity modifier such as sodium chloride, sodium sulphate, sodium acetate, sodium lactate, glycine, histidine, or arginine, at a concentration of about 25 mM to about 500 mM such as about 50 mM to about 250 mM, and/or
  (iv) a preservative such as phenol, m-cresol, chlorocresol, benzyl alcohol, propylparaben, methylparaben, benzalkonium chloride, or benzethonium chloride, at a concentration of about 0.01 mM to about 100 mM.

In some embodiments, the conductivity of the aqueous solution is >2.5 mS/cm. In some embodiments, the conductivity of the aqueous solution is <2.5 mS/cm.

In some embodiments, the aqueous solution of the invention comprises,
(a) a bispecific antibody (e.g. an antibody that binds CD3 and another antigen, such as blinatumomab) at a concentration of about 1 mg/mL to about 300 mg/mL (e.g. about 10 mg/mL to about 300 mg/mL, about 1 mg/mL to about 200 mg/mL, about 10 mg/mL to about 200 mg/mL, about 25 mg/mL to about 75 mg/mL, about 80 mg/mL to about 125, about 130 mg/mL to about 180 mg/mL, or about 190 mg/mL to about 250 mg/mL, or about 50 mg/mL, about 100 mg/mL, about 150 mg/mL, about 160 mg/mL, about 200 mg/mL, or about 240 mg/mL); and
(b) a stabilizing amount of
  (i) 1,2-propanediol or glycerol, or a mixture thereof, at a concentration of about 100 mM to about 500 mM (e.g. about 150 mM to about 400 mM, about 150 mM to about 350 mM, or about 200 mM to about 300 mM, or about 200 mg/mL, about 250 mg/mL, or about 300 mg/mL),
  (ii) arginine (e.g. L arginine) at a concentration of about 5 mM to about 150 mM, (e.g. about 5 mM to about 100 mM, about 20 mM to about 125 mM, about 60 mM to about 120 mM, about 60 mM to about 100 mM, or about 20 mM to about 80 mM, or about 50 mM, about 60 mM, about 80 mM, about 100 mM, or about 150 mM), and
  (iii) methionine (e.g. L methionine) at a concentration of 2 mM to about 75 mM (e.g. 2 mM to about 50 mM, or about 10 mM to about 40 mM, or about 30 mM);
  optionally, wherein the ratio (mM/mM) of arginine to methionine is between about 1:1 and about 10:1 (e.g. between about 2:1 and about 6:1), the ratio (mM/mM) of arginine to C3 polyol is between about 2:1 and 1:20 (e.g. between about 1:2 and about 1:10), the ratio (mM/mM) of methionine to C3 polyol is between about 1:1 and 1:40 (e.g. between about 1:4 and about 1:20), the ratio (mM/mM) of the combined concentration of arginine and methionine to C3 polyol is between about 4:1 and 1:20 (e.g. between about 2:1 and about 1:10), the ratio (wt/wt) of antibody protein to the combined weight of arginine and methionine is between about 1:15 and about 30:1 (e.g. between about 1:1 and about 25:1), or between about 1:2 and about 50:1 (e.g. between about 2:1 and about 25:1), and/or the ratio (wt/wt) of antibody protein to C3 polyol is between about 1:5 and about 200:1 (e.g. between about 2:1 and about 50:1) or between about 1:2 and about 200:1 (e.g. between about 2:1 and about 50:1); and wherein the pH of the aqueous solution is between about pH 4.0 and about pH 8.0 (e.g. between about pH 5.0 and about pH 7.0 or between about pH 5.0 and about pH 6.5); optionally wherein the aqueous solution further comprises (i) a buffer (e.g. histidine, succinate, maleate, acetate, phosphate or TRIS) at a concentration of about 0.5 mM to about 50 mM (e.g. about 1 mM to about 20 mM, about 2 mM to about 10 mM, or about 2 mM to about 5 mM), (ii) a non-ionic surfactant (e.g. an alkyl glycoside, such as dodecyl maltoside, a polysorbate surfactant, such as polysorbate 80, or polysorbate 20, an alkyl ether of polyethylene glycol, such as polyethylene glycol (2) dodecyl ether, polyethylene glycol (2) oleyl ether or polyethylene glycol (2) hexadecyl ether, a block copolymer of polyethylene glycol and polypropylene glycol, such as poloxamer 188, poloxamer 407, poloxamer 171, or poloxamer 185, or an alkylphenyl ether of polyethylene glycol, such as 4-(1,1,3,3-tetramethylbutyl) phenyl-polyethylene glycol, at a concentration of about 10 μg/mL to about 2000 μg/mL (e.g. about 50 μg/mL to about 1500 μg/mL, about 50 μg/mL to about 1250 μg/mL, about 50 μg/mL to about 1000 μg/mL, about 100 μg/mL to about 750 μg/mL, or about 100 μg/mL to about 500 μg/mL, or about 500 μg/mL, about 750 μg/mL, about 1000 μg/mL, about 1250 μg/mL, or about 1500 μg/mL), (iii) a tonicity modifier (e.g. an uncharged tonicity modifier, such as sucrose, trehalose, mannitol, sorbitol, PEG300, or PEG400, at a concentration of about 50 mM to about 1000 mM, such as about 100 mM to about 500 mM), or a charged tonicity modifier such as sodium chloride, sodium sulphate, sodium acetate, sodium lactate, glycine, histidine, or arginine, at a concentration of about 25 mM to about 500 mM such as about 50 mM to about 250 mM, and/or (iv) a preservative such as phenol, m-cresol, chlorocresol, benzyl alcohol, propylparaben, methylparaben, benzalkonium chloride, or benzethonium chloride, at a concentration of about 0.01 mM to about 100 mM.

In some embodiments, the conductivity of the aqueous solution is >2.5 mS/cm. In some embodiments, the conductivity of the aqueous solution is <2.5 mS/cm.

In some embodiments, the aqueous solution of the invention comprises, (a) a fusion protein comprising an active protein domain fused to one or more immunoglobulin Fc fragments (e.g. a peptibody, abatacept, or belatacept) at a concentration of about 1 mg/mL to about 300 mg/mL (e.g. about 10 mg/mL to about 300 mg/mL, about 1 mg/mL to about 200 mg/mL, about 10 mg/mL to about 200 mg/mL, about 25 mg/mL to about 75 mg/mL, about 80 mg/mL to about 125, about 130 mg/mL to about 180 mg/mL, or about 190 mg/mL to about 250 mg/mL, or about 50 mg/mL, about 100 mg/mL, about 150 mg/mL, about 160 mg/mL, about 200 mg/mL, or about 240 mg/mL); and (b) a stabilizing amount of (i) 1,2-propanediol or glycerol, or a mixture thereof, at a concentration of about 100 mM to about 500 mM (e.g. about 150 mM to about 400 mM, about 150 mM to about 350 mM, or about 200 mM to about 300 mM, or about 200 mg/mL, about 250 mg/mL, or about 300 mg/mL), (ii) arginine (e.g. L arginine) at a concentration of about 5 mM to about 150 mM, (e.g. about 5 mM to about 100 mM, about 20 mM to about 125 mM, about 60 mM to about 120 mM, about 60 mM to about 100 mM, or about 20 mM to about 80 mM, or about 50 mM, about 60 mM, about 80 mM, about 100 mM, or about 150 mM), and (iii) methionine (e.g. L methionine) at a concentration of 2 mM to about 75 mM (e.g. 2 mM to about 50 mM, or about 10 mM to about 40 mM, or about 30 mM);

optionally, wherein the ratio (mM/mM) of arginine to methionine is between about 1:1 and about 10:1 (e.g. between about 2:1 and about 6:1), the ratio (mM/mM) of arginine to C3 polyol is between about 2:1 and 1:20 (e.g. between about 1:2 and about 1:10), the ratio (mM/mM) of methionine to C3 polyol is between about 1:1 and 1:40 (e.g. between about 1:4 and about 1:20), the ratio (mM/mM) of the combined concentration of arginine and methionine to C3 polyol is between about 4:1 and 1:20 (e.g. between about 2:1 and about 1:10), the ratio (wt/wt) of antibody protein to the combined weight of arginine and methionine is between about 1:15 and about 30:1 (e.g. between about 1:1 and about 25:1), or between about 1:2 and about 50:1 (e.g. between about 2:1 and about 25:1), and/or the ratio (wt/wt) of antibody protein to C3 polyol is between about 1:5 and about 200:1 (e.g. between about 2:1 and about 50:1) or between about 1:2 and about 200:1 (e.g. between about 2:1 and about 50:1); and wherein the pH of the aqueous solution is between about pH 4.0 and about pH 8.0 (e.g. between about pH 5.0 and about pH 7.0 or between about pH 5.0 and about pH 6.5); optionally wherein the aqueous solution further comprises (i) a buffer (e.g. histidine, succinate, maleate, acetate, phosphate or TRIS) at a concentration of about 0.5 mM to about 50 mM (e.g. about 1 mM to about 20 mM, about 2 mM to about 10 mM, or about 2 mM to about 5 mM), (ii) a non-ionic surfactant (e.g. an alkyl glycoside, such as dodecyl maltoside, a polysorbate surfactant, such as polysorbate 80, or polysorbate 20, an alkyl ether of polyethylene glycol, such as polyethylene glycol (2) dodecyl ether, polyethylene glycol (2) oleyl ether or polyethylene glycol (2) hexadecyl ether, a block copolymer of polyethylene glycol and polypropylene glycol, such as poloxamer 188, poloxamer 407, poloxamer 171, or poloxamer 185, or an alkylphenyl ether of polyethylene glycol, such as 4-(1,1,3,3-tetramethylbutyl) phenyl-polyethylene glycol, at a concentration of about 10 μg/mL to about 2000 μg/mL (e.g. about 50 μg/mL to about 1500 μg/mL, about 50 μg/mL to about 1250 μg/mL, about 50 μg/mL to about 1000 μg/mL, about 100 μg/mL to about 750 μg/mL, or about 100 μg/mL to about 500 μg/mL, or about 500 μg/mL, about 750 μg/mL, about 1000 μg/mL, about 1250 μg/mL, or about 1500 μg/mL), (iii) a tonicity modifier (e.g. an uncharged tonicity modifier, such as sucrose, trehalose, mannitol, sorbitol, PEG300, or PEG400, at a concentration of about 50 mM to about 1000 mM, such as about 100 mM to about 500 mM), or a charged tonicity modifier such as sodium chloride, sodium sulphate, sodium acetate, sodium lactate, glycine, histidine, or arginine, at a concentration of about 25 mM to about 500 mM such as about 50 mM to about 250 mM, and/or (iv) a preservative such as phenol, m-cresol, chlorocresol, benzyl alcohol, propylparaben, methylparaben, benzalkonium chloride, or benzethonium chloride, at a concentration of about 0.01 mM to about 100 mM.

In some embodiments, the conductivity of the aqueous solution is >2.5 mS/cm. In some embodiments, the conductivity of the aqueous solution is <2.5 mS/cm.

In some embodiments, the aqueous solution of the invention comprises,
(a) etanercept at a concentration of about 1 mg/mL to about 300 mg/mL (e.g. about 10 mg/mL to about 300 mg/mL, about 1 mg/mL to about 200 mg/mL, about 10 mg/mL to about 200 mg/mL, about 25 mg/mL to about 75 mg/mL, about 80 mg/mL to about 125, about 130 mg/mL to about 180 mg/mL, or about 190 mg/mL to about 250 mg/mL, or about 50 mg/mL, about 100 mg/mL, about 150 mg/mL, about 160 mg/mL, about 200 mg/mL, or about 240 mg/mL); and
(b) a stabilizing amount of
  (i) 1,2-propanediol or glycerol, or a mixture thereof, at a concentration of about 100 mM to about 500 mM (e.g. about 150 mM to about 400 mM, about 150 mM to about 350 mM, or about 200 mM to about 300 mM, or about 200 mg/mL, about 250 mg/mL, or about 300 mg/mL),
  (ii) arginine (e.g. L arginine) at a concentration of about 5 mM to about 150 mM, (e.g. about 5 mM to about 100 mM, about 20 mM to about 125 mM, about 60 mM to about 120 mM, about 60 mM to about 100 mM, or about 20 mM to about 80 mM, or about 50 mM, about 60 mM, about 80 mM, about 100 mM, or about 150 mM), and
  (iii) methionine (e.g. L methionine) at a concentration of 2 mM to about 75 mM (e.g. 2 mM to about 50 mM, or about 10 mM to about 40 mM, or about 30 mM);
  optionally, wherein the ratio (mM/mM) of arginine to methionine is between about 1:1 and about 10:1 (e.g. between about 2:1 and about 6:1), the ratio (mM/mM) of arginine to C3 polyol is between about 2:1 and 1:20 (e.g. between about 1:2 and about 1:10), the ratio (mM/mM) of methionine to C3 polyol is between about 1:1 and 1:40 (e.g. between about 1:4 and about 1:20), the ratio (mM/mM) of the combined concentration of arginine and methionine to C3 polyol is between about 4:1 and 1:20 (e.g. between about 2:1 and about 1:10), the ratio (wt/wt) of antibody protein to the combined weight of arginine and methionine is between about 1:15 and about 30:1 (e.g. between about 1:1 and about 25:1), or between about 1:2 and about 50:1 (e.g. between about 2:1 and about 25:1), and/or the ratio (wt/wt) of antibody protein to C3 polyol is between about 1:5 and about 200:1 (e.g. between about 2:1 and about 50:1) or between about 1:2 and about 200:1 (e.g. between about 2:1 and about 50:1);
wherein the pH of the aqueous solution is between about pH 4.0 and about pH 8.0 (e.g. between about pH 5.0 and about pH 7.0 or between about pH 5.0 and about pH 6.5);
optionally wherein the aqueous solution further comprises
  (i) a buffer (e.g. histidine, succinate, maleate, acetate, phosphate or TRIS) at a concentration of about 0.5 mM to about 50 mM (e.g. about 1 mM to about 20 mM, about 2 mM to about 10 mM, or about 2 mM to about 5 mM),
  (ii) a non-ionic surfactant (e.g. an alkyl glycoside, such as dodecyl maltoside, a polysorbate surfactant, such as polysorbate 80, or polysorbate 20, an alkyl ether of polyethylene glycol, such as polyethylene glycol (2) dodecyl ether, polyethylene glycol (2) oleyl ether or polyethylene glycol (2) hexadecyl ether, a block copolymer of polyethylene glycol and polypropylene glycol, such as poloxamer 188, poloxamer 407, poloxamer 171, or poloxamer 185, or an alkylphenyl ether of polyethylene glycol, such as 4-(1,1,3,3-tetramethylbutyl) phenyl-polyethylene glycol, at a concentration of about 10 µg/mL to about 2000 µg/mL (e.g. about 50 µg/mL to about 1500 µg/mL, about 50 µg/mL to about 1250 µg/mL, about 50 µg/mL to about 1000 µg/mL, about 100 µg/mL to about 750 µg/mL, or about 100 µg/mL to about 500 µg/mL, or about 500 µg/mL, about 750 µg/mL, about 1000 µg/mL, about 1250 µg/mL, or about 1500 µg/mL),
  (iii) a tonicity modifier (e.g. an uncharged tonicity modifier, such as sucrose, trehalose, mannitol, sorbitol, PEG300, or PEG400, at a concentration of about 50 mM to about 1000 mM, such as about 100 mM to about 500 mM), or a charged tonicity modifier such as sodium chloride, sodium sulphate, sodium acetate, sodium lactate, glycine, histidine, or arginine, at a concentration of about 25 mM to about 500 mM such as about 50 mM to about 250 mM, and/or
  (iv) a preservative such as phenol, m-cresol, chlorocresol, benzyl alcohol, propylparaben, methylparaben, benzalkonium chloride, or benzethonium chloride, at a concentration of about 0.01 mM to about 100 mM.

In some embodiments, the conductivity of the aqueous solution is >2.5 mS/cm. In some embodiments, the conductivity of the aqueous solution is <2.5 mS/cm.

The present inventors have discovered that when a C3 polyol is added to an aqueous solution comprising an antibody protein, arginine and methionine, the stability of the antibody protein is surprisingly enhanced. Without wishing to be bound by theory it is believed that the additional stabilising effect of a C3 polyol is due to optimal hydrophobic and hydrogen bond interactions at the protein surface of the small polyols leading to tighter conformation and modified interfacial tension between the protein molecules, in turn leading to lower exposure of reaction sites as well as lower probability of irreversible aggregation events.

The C3 polyol is suitably selected from 1,2-propanediol (also known as propane-1,2-diol or propylene glycol) and glycerol (also known as 1,2,3-propanetriol, glycerin or glycerine). In one embodiment, the C3 polyol is 1,2-propanediol. In another embodiment, the C3 polyol is glycerol. In a further embodiment, the C3 polyol is a mixture of 1,2-propanediol and glycerol. The C3 polyol is suitably present at a concentration of about 100 mM to about 500 mM, such as about 150 mM to about 400 mM, or about 150 mM to about 200 mM. If more than one C3 polyol is present in the aqueous solution, then the concentration refers to the total concentration of C3 polyols.

In one embodiment, the ratio (mM/mM) of arginine to methionine is about between about 1:1 and about 10:1 e.g. between about 2:1 and about 6:1.

In one embodiment, the ratio (mM/mM) of arginine to C3 polyol is between about 2:1 and 1:20 e.g. between about 1:2 and about 1:10.

In one embodiment, the ratio (mM/mM) of methionine to C3 polyol is between about 1:1 and 1:40 e.g. between about 1:4 and about 1:20.

In one embodiment, the ratio (mM/mM) of the combined concentration of arginine and methionine to C3 polyol is between about 4:1 and 1:20 e.g. between about 2:1 and about 1:10.

In one embodiment, the ratio (wt/wt) of antibody protein to arginine is between about 1:10 and about 100:1 e.g. between about 1:1 and about 40:1. In another embodiment, the ratio (wt/wt) of antibody protein to arginine is between about 1:1 and about 100:1 e.g. between about 5:1 and about 40:1.

In one embodiment, the ratio (wt/wt) of antibody protein to methionine is between about 1:5 and about 200:1 e.g. between about 2:1 and about 80:1. In another embodiment, the ratio (wt/wt) of antibody protein to methionine is between about 2:1 and about 200:1 e.g. between about 10:1 and about 80:1.

In one embodiment, the ratio (wt/wt) of antibody protein to the combined weight of arginine and methionine is between about 1:15 and about 30:1 e.g. between about 1:1 and about 25:1. In another embodiment, the ratio (wt/wt) of antibody protein to the combined weight of arginine and methionine is between about 1:2 and about 50:1 e.g. between about 2:1 and about 25:1.

In one embodiment, the ratio (wt/wt) of antibody protein to C3 polyol is between about 1:5 and about 200:1 e.g. between about 2:1 and about 50:1. In another embodiment, the ratio (wt/wt) of antibody protein to C3 polyol is between about 1:2 and about 200:1 e.g. between about 2:1 and about 50:1.

The addition of a mixture of arginine, methionine and a C3 polyol to an aqueous solution of antibody protein is expected to enhance the stability of the antibody protein, e.g. as shown in Example 1. The mixture of arginine, methionine and a C3 polyol is thus referred to as a stabilizing mixture.

The "stability" of an antibody protein or a "stabilizing mixture" typically refers to a reduction of antibody protein degradation during storage. In one embodiment, "stability"/"stabilizing" refers to physical stability e.g. loss of quaternary, tertiary or secondary structure, aggregation or particle formation. In another embodiment, "stability"/"stabilizing" refers to chemical stability e.g. processes involving a covalent change such as deamidation, aspartate isomerization, oxidation or hydrolytic clipping.

It is expected that the addition of a C3 polyol to an aqueous solution comprising an antibody protein, arginine and methionine can enhance the stability of the antibody protein and in particular reduce the rate of antibody protein aggregation, compared with the same solution lacking the C3 polyol, following storage under the same conditions for the same length of time.

The present invention thus provides a method of stabilizing an antibody protein in an aqueous solution to storage comprising the step of adding to the solution a mixture of arginine, methionine and a C3 polyol. Also provided is the use of a mixture of arginine, methionine and a C3 polyol for stabilizing an antibody protein in an aqueous solution to storage. All embodiments described hereinabove with reference to the aqueous solution of the invention apply equally to the method and use of the invention.

In some embodiments, the method of the invention refers to adding arginine, methionine and a C3 polyol (e.g. 1,2-propanediol or glycerol) to an aqueous solution containing a an aqueous solution containing an antibody protein. In some embodiments, the method of the invention refers to "the step of adding to the solution a mixture of arginine, methionine and a C3 polyol". It should be understood that the arginine, methionine and C3 polyol can be added to the solution all together at the same time, or sequentially, and in any order (i.e. "the step" may actually include multiple steps).

The disclosure provides a method for inhibiting formation of high molecular weight species of an antibody protein in aqueous solution during storage comprising, adding (i) a chelating agent which is a multi-anion (e.g. EDTA); and (ii) a C3 polyol (e.g. glycerol and/or propylene glycol) to the aqueous solution. Also provided is a method for inhibiting formation of high molecular weight species of an antibody protein in aqueous solution during storage, comprising the step of adding to the solution a mixture of arginine, methionine and a C3 polyol.

The disclosure provides a method for inhibiting formation of visible particles in an aqueous solution of an antibody protein during storage comprising, adding (i) a chelating agent which is a multi-anion (e.g. EDTA); and (ii) a C3 polyol (e.g. glycerol and/or propylene glycol) to the aqueous solution. Also provided is a method for inhibiting formation of visible particles in a solution of an antibody protein during storage, comprising the step of adding to the solution a mixture of arginine, methionine and a C3 polyol.

The disclosure provides a method for inhibiting formation of related species of an antibody protein in aqueous solution during storage, comprising adding (i) a chelating agent which is a multi-anion (e.g. EDTA); and (ii) a C3 polyol (e.g. glycerol and/or propylene glycol) to the aqueous solution. Also provided is a method for inhibiting formation of related species of an antibody protein in aqueous solution during storage, comprising the step of adding to the solution a mixture of arginine, methionine and a C3 polyol.

The disclosure provides a method for inhibiting deamidation of an antibody protein in aqueous solution during storage, comprising adding (i) a chelating agent which is a multi-anion (e.g. EDTA); and (ii) a C3 polyol (e.g. glycerol and/or propylene glycol) to the aqueous solution. Also provided is a method for inhibiting deamidation of an antibody protein in aqueous solution during storage, comprising the step of adding to the solution a mixture of arginine, methionine and a C3 polyol.

The disclosure provides a method for inhibiting the formation of low molecular weight degradation products in an aqueous solution of an antibody protein during storage, comprising adding (i) a chelating agent which is a multi-anion (e.g. EDTA); and (ii) a C3 polyol (e.g. glycerol and/or propylene glycol) to the aqueous solution. Also provided is a method for inhibiting the formation of low molecular weight degradation products in an aqueous solution of an antibody protein during storage, comprising the step of adding to the solution a mixture of arginine, methionine and a C3 polyol.

Also provided is the use of a mixture of arginine, methionine and a C3 polyol for inhibiting the formation of high molecular weight species of an antibody protein in aqueous solution during storage.

Also provided is the use of a mixture of arginine, methionine and a C3 polyol for inhibiting the formation of visible particles in a composition of an antibody protein in aqueous solution during storage.

Also provided is the use of a mixture of arginine, methionine and a C3 polyol for inhibiting formation of related species of an antibody protein in aqueous solution during storage.

Also provided is the use of a mixture of arginine, methionine and a C3 polyol for inhibiting deamidation of an antibody protein in aqueous solution during storage.

Also provided is the use of a mixture of arginine, methionine and a C3 polyol for inhibiting formation of low molecular weight degradation products in an aqueous solution of an antibody protein during storage.

The term "high molecular weight species" as used herein, refers to any component of the antibody protein content which has an apparent molecular weight at least about double the molecular weight of the parent active antibody protein. That is, high molecular weight species are multimeric aggregates of the parent antibody protein. The multimeric aggregates may comprise the parent antibody protein molecules with considerably altered conformation or they may be an assembly of the parent protein units in the native or near-native conformation. The determination of high molecular weight species can be done using methods known in the art, including size exclusion chromatography, electrophoresis, analytical ultracentrifugation/sedimentation velocity, light scattering, dynamic light scattering, static light scattering and field flow fractionation.

The term "low molecular weight degradation products" as used herein, refers to any component of the antibody protein content which has an apparent molecular weight less than the molecular weight of the parent active antibody protein. That is, low molecular weight degradation products are fragments of the parent antibody protein. The determination of high molecular weight species can be done using methods known in the art, including size exclusion chromatography, electrophoresis, analytical ultracentrifugation/sedimentation velocity, light scattering, dynamic light scattering, static light scattering and field flow fractionation.

The term "related species" as used herein, refers to any component of the antibody protein content formed by a chemical modification of the parent antibody protein, such as deamidated species or oxidised species. Related species are suitably detected by cation-exchange chromatography, reversed-phase chromatography or capillary electrophoresis.

Suitably an aqueous solution of the invention is sufficiently stable such that it remains substantially free of visible particles after storage at 30° C. for at least one, two or three months. Visible particles are suitably detected using the 2.9.20. European Pharmacepoeia Monograph (Particulate Contamination: Visible Particles).

Suitably the aqueous solution of the invention is sufficiently stable such that the concentration of related species remains low upon extended storage.

In one embodiment, the aqueous solution of the invention retains at least 95%, e.g. at least 96%, e.g. at least 97%, e.g. at least 98%, e.g. at least 99% parent antibody protein (by weight of total antibody protein) after storage at 30° C. for one, two or three months. The percentage of antibody protein (by weight of total antibody protein) may be determined by size-exclusion chromatography, cation-exchange chromatography, reversed-phase chromatography or capillary electrophoresis.

In one embodiment, the presence of a mixture of arginine, methionine and a C3 polyol limits the increase in high molecular weight antibody protein species to no more than 5% (by weight of total antibody protein) after storage at 40° C. for one month, suitably to no more than 3% and more suitably to no more than 2%. In one embodiment, the presence of a mixture of arginine, methionine and a C3 polyol limits the increase in high molecular weight antibody protein species to no more than 5% (by weight of total antibody protein) after storage at 2-8° C. for up to two years, suitably to no more than 3% and more suitably to no more than 2%. Quantitation of high molecular weight species is as percent by weight of the total antibody protein in the aqueous solution.

In one embodiment, the presence of a mixture of arginine, methionine, and a C3 polyol limits the increase in high molecular weight antibody protein species by at least 10%, preferably by at least 25%, and more preferably by at least 50% compared with an aqueous solution lacking the mixture of arginine, methionine, and a C3 polyol but otherwise identical, following storage under the same conditions and length of time.

In one embodiment, the presence of a mixture of arginine, methionine and C3 polyol maintains an aqueous solution of an antibody protein free of visible aggregates while formation of visible aggregates is observed in an aqueous solution lacking the mixture of arginine, methionine and C3 polyol but otherwise identical, following storage under the same conditions and for the same length of time. Quantification of visible aggregates can be performed by turbidity or other types of light scattering measurement.

Suitably, the aqueous solution of the invention comprises no more than 5% (by weight of total protein) high molecular weight species after storage at 40° C. for at least one, two or three months. In one embodiment, the amount of high molecular weight species increases by no more than 5% (by weight of total antibody protein), preferably no more than 3%, after storage at 40° C. for at least one, two or three months. Quantitation of high molecular weight species is as percent by weight of the total antibody protein in the aqueous solution.

Suitably, the aqueous solution of the invention should exhibit an increase in high molecular weight species during storage which is at least 10% lower, preferably at least 25% lower, more preferably at least 50% lower, than an aqueous solution lacking the mixture of arginine, methionine and C3 polyol but otherwise identical, following storage under the same conditions and length of time.

In one embodiment, the aqueous solution of the invention is a pharmaceutical composition suitable for administration of a therapeutic antibody protein to a subject in need thereof. Such compositions can be used in a method for administering the therapeutic protein to the subject.

In another embodiment, the invention provides a method for administering a therapeutic antibody protein to a subject in need thereof. The method comprises the step of administering an aqueous solution comprising the antibody protein, arginine, methionine and a C3 polyol. Preferably the composition is administered by intravenous, subcutaneous or intramuscular injection, or infusion. More preferably the composition is administered by subcutaneous injection.

In another embodiment, the invention provides a packaged pharmaceutical composition suitable for administration to a subject in need thereof. The pharmaceutical composition comprises an aqueous solution comprising an antibody protein, arginine, methionine and a C3 polyol. The pharmaceutical composition is preferably packaged in a vial suitable for introduction of a needle for removal of the solution. In one embodiment, the pharmaceutical composition is packaged in a glass vial with a rubber stopper. The packaged pharmaceutical composition can be provided as a kit, further comprising instructions for use and, optionally, a syringe suitable for intramuscular or subcutaneous administration. Alternatively, the packaged pharmaceutical composition can be provided in the form of a pre-filled disposable syringe suitable for intramuscular or subcutaneous administration. A pre-filled auto-injector device would also be suitable for intramuscular or subcutaneous administration.

The term "pharmaceutically acceptable", as used herein, refers to components of a pharmaceutical composition which are suitable for the intended use and mode of administration to the body of a human or an animal, such as a mammal, without undue adverse consequences, such as toxicity, irritation, and allergic response and with a reasonable risk/benefit ratio.

Abbreviations
PEG polyethylene glycol
HMWS high molecular weight specie
SEC size exclusion chromatography
CEX cation-exchange chromatography

EXAMPLES

Materials

Arginine (Mw 174 Da), methionine (Mw 149 Da), 1,2-propanediol (Mw 76 Da), glycerol (Mw 92 Da), mannitol (Mw 182 Da), NaCl (Mw 58 Da), trehalose (Mw 342 Da) were obtained from Sigma Aldrich.

Methods of Assessing Stability of an Antibody Protein (a) Visual Assessment

Visible particles are suitably detected using the 2.9.20. European Pharmacepoeia Monograph (Particulate Contamination: Visible Particles). The apparatus required consists of a viewing station comprising:
- a matt black panel of appropriate size held in a vertical position
- a non-glare white panel of appropriate size held in a vertical position next to the black panel
- an adjustable lampholder fitted with a suitable, shaded, white-light source and with a suitable light diffuser (a viewing illuminator containing two 13 W fluorescent tubes, each 525 mm in length, is suitable). The intensity of illumination at the viewing point is maintained between 2000 lux and 3750 lux.

Any adherent labels are removed from the container and the outside washed and dried. The container is gently swirled or inverted, ensuring that air bubbles are not introduced, and observed for about 5 s in front of the white panel. The procedure is repeated in front of the black panel. The presence of any particles is recorded.

The visual scores are ranked as follows:
Visual score 1: Clear solution, virtually free of particles
Visual score 2: ~5 very small particles
Visual score 3: ~10-20 very small particles
Visual score 4: 20-50 particles, including larger particles
Visual score 5: >50 particles, including larger particles Whilst the particles in samples with visual scores 4 and 5 are clearly detectable on casual visual assessment under normal light, samples with visual score 1-3 generally appear as clear solutions on the same assessment. Samples with visual scores 1-3 are considered to be "Pass"; samples with visual score 4-5 are considered to be "Fail".

(b) Size Exclusion Chromatography (SEC)

The amount of high molecular weight species is measured using a 300×7.8 mm S3000 (or equivalent) size-exclusion column with a guard column. The mobile phase is potassium phosphate pH 6.5, with a flow rate of 0.4 ml/min, injection volume of 1 µl and detected at 210 and 280 nm. The results are expressed as % high molecular species (HMWS), i.e. sum of all peak areas corresponding to aggregated protein over the sum of all protein-related peaks on the chromatogram. A small time-point to time-point variability can be observed in terms of absolute values of % HMWS, for example due to repeated size-exclusion column use. However, within a given time-point the samples are tested using the column in the same condition, so the values generated within the time-point represent a very good indication of the relative stability of the protein in the aqueous solutions tested.

(c) Cation-Exchange Chromatography Chromatography (CEX)

The amount of related species is measured using a Protein-Pak Hi Res SP column. Mobile phase A is 20 mM sodium phosphate (pH 6.5); mobile phase B is 20 mM sodium phosphate+0.5 M NaCl (pH 6.0). The following gradient elution is used: 0 min-100% A, 4 min-80% A, 10 min-55% A, 12 min-0% A. Flow rate of 1.0 ml/min; injection volume is 3 µl, with UV detection at 214 nm. The results are expressed as % main peak (i.e. native protein), % acidic species and % basic species. % Related species=% acidic species+% basic species.

Example 1

The effect of arginine, methionine and C3 polyols on the stability of rituximab (10 mg/ml) was investigated. The effect was tested in a background solution containing trisodium citrate (5 mM) and polysorbate 80 (0.7 mg/ml). All formulations tested (F1-F20) were adjusted to pH 6.5. Additional excipients in the formulations tested are shown in Table 1.

TABLE 1

Additional components in formulations (F1-F20) of rituximab tested. All formulations contained rituximab (10 mg/ml), trisodium citrate (5 mM) and polysorbate 80 (0.7 mg/ml) and were adjusted to pH 6.5.

|  | Glycerol (mM) | 1,2-propanediol (mM) | Sucrose (mM) | Trehalose (mM) | NaCl (mM) | Methionine (mM) | Arginine (mM) |
|---|---|---|---|---|---|---|---|
| F1 | 150 | | | | | | |
| F2 | 150 | | | | | | 80 |
| F3 | 150 | | | | | 30 | |
| F4 | 150 | | | | | 30 | 80 |
| F5 | | 300 | | | | | |
| F6 | | 300 | | | | | 80 |
| F7 | | 300 | | | | 30 | |
| F8 | | 300 | | | | 30 | 80 |
| F9 | | | 300 | | | | |
| F10 | | | 300 | | | | 80 |
| F11 | | | 300 | | | 30 | |
| F12 | | | 300 | | | 30 | 80 |
| F13 | | | | 300 | | | |
| F14 | | | | 300 | | | 80 |
| F15 | | | | 300 | | 30 | |
| F16 | | | | 300 | | 30 | 80 |
| F17 | | | | | 300 | | |
| F18 | | | | | 300 | | 80 |
| F19 | | | | | 300 | 30 | |
| F20 | | | | | 300 | 30 | 80 |

Stability of Formulations F1-F20 was tested at 40° C. by visual assessment and size-exclusion chromatography (SEC) as described above. Results are shown in Table 2. It was shown that addition of arginine alone led to improved visual score as well as a slight reduction in the rate of HMWS formation following storage of rituximab at 40° C. in the presence of all tonicity modifiers tested (glycerol, 1,2-propanediol, sucrose, trehalose and sodium chloride). The addition of methionine alone did not appear to affect the visual score and led to a slight reduction in the rate of HMWS formation in the presence of the uncharged tonicity modifiers (glycerol, 1,2-propanediol, sucrose, trehalose), but not in the presence of sodium chloride. However, the best results (i.e. visual score 1 and the lowest rate of HMWS formation) were achieved if both arginine and methionine were added in the presence of C3 polyols. The stability of rituximab was better in these compositions (Formulations F4 and F8) than in any other compositions tested.

TABLE 2

Stability of rituximab (10 mg/ml) in Formulations F1-F20 assessed by SEC and visual assessment. Formation of HMWS was assessed following storage at 40° C. for 4 and 8 weeks. Visual score 1: clear solution, virtually free of particles; visual score 2: ~5 very small particles; visual score 3: ~10-20 very small particles; visual score 4: 20-50 particles, including larger particles; visual score 5: >50 particles, including larger particles.

| Formulation | Increase (from T0) in % HMWS (4 weeks) | Visual assessment (4 weeks) | Increase (from T0) in % HMWS (8 weeks) | Visual assessment (8 weeks) |
|---|---|---|---|---|
| F1 | 0.86 | 2 | 1.84 | 3 |
| F2 | 0.50 | 1 | 0.96 | 2 |
| F3 | 0.58 | 2 | 1.16 | 3 |
| F4 | 0.19 | 1 | 0.42 | 1 |
| F5 | 0.79 | 3 | 1.71 | 3 |
| F6 | 0.54 | 1 | 0.91 | 1 |
| F7 | 0.50 | 2 | 1.11 | 3 |
| F8 | 0.28 | 1 | 0.50 | 1 |
| F9 | 0.62 | 2 | 1.51 | 3 |
| F10 | 0.44 | 1 | 0.96 | 1 |
| F11 | 0.46 | 2 | 1.05 | 3 |
| F12 | 0.42 | 1 | 0.79 | 2 |
| F13 | 0.69 | 2 | 1.54 | 3 |
| F14 | 0.59 | 1 | 1.06 | 1 |
| F15 | 0.63 | 2 | 1.24 | 3 |
| F16 | 0.67 | 2 | 1.00 | 1 |
| F17 | 0.67 | 2 | 1.50 | 3 |
| F18 | 0.57 | 1 | 1.22 | 3 |
| F19 | 0.72 | 3 | 1.48 | 3 |
| F20 | 0.74 | 2 | 1.36 | 3 |

Example 2

The effect of arginine, methionine and C3 polyols on the stability of adalimumab (50 mg/ml, 100 mg/ml, 160 mg/ml, 200 mg/ml, and 240 mg/ml) is investigated at 40° C., 25° C., and 2-8° C. The effect is tested in a background solution containing sodium acetate (8 mM) and polysorbate 20 (1 mg/ml). All formulations tested (F1-F20) are adjusted to pH 5.2. Additional excipients in the formulations tested are shown in Table 3.

TABLE 3

Additional components in formulations of adalimumab tested. One set of formulations (F1-F16) is conducted for each evaluated concentration of adalimumab (50 mg/ml, 100 mg/ml, 160 mg/ml, 200 mg/ml, and 240 mg/ml). All formulations contain adalimumab, sodium acetate (8 mM) and polysorbate 20 (1 mg/ml) and are adjusted to pH 5.2.

| | Glycerol (mM) | 1,2-propanediol (mM) | Methionine (mM) | Arginine (mM) |
|---|---|---|---|---|
| F1 | 130 | | | |
| F2 | 130 | | | 60 |
| F3 | 130 | | | 100 |
| F4 | 130 | | | 150 |
| F5 | 130 | | 30 | |
| F6 | 130 | | 30 | 60 |
| F7 | 130 | | 30 | 100 |
| F8 | 130 | | 30 | 150 |
| F9 | | 130 | | |
| F10 | | 130 | | 60 |
| F11 | | 130 | | 100 |
| F12 | | 130 | | 150 |
| F13 | | 130 | 30 | |
| F14 | | 130 | 30 | 60 |
| F15 | | 130 | 30 | 100 |
| F16 | | 130 | 30 | 150 |

Thus, exemplary formulations prepared in this example include aqueous solutions containing:

(a) adalimumab (50 mg/ml, 100 mg/ml, 160 mg/ml, 200 mg/ml, or 240 mg/ml), glycerol (130 mM), methionine (30 mM), arginine (60 mM, 100 mM, or 150 mM), sodium acetate (8 mM), and polysorbate 20 (1 mg/ml) at pH 5.2, e.g.
  (i) adalimumab (50 mg/ml), glycerol (130 mM), methionine (30 mM), arginine (60 mM, 100 mM, or 150 mM), sodium acetate (8 mM), and polysorbate 20 (1 mg/ml) at pH 5.2;
  (ii) adalimumab (100 mg/ml), glycerol (130 mM), methionine (30 mM), arginine (60 mM, 100 mM, or 150 mM), sodium acetate (8 mM), and polysorbate 20 (1 mg/ml) at pH 5.2;
  (iii) adalimumab (160 mg/ml), glycerol (130 mM), methionine (30 mM), arginine (60 mM, 100 mM, or 150 mM), sodium acetate (8 mM), and polysorbate 20 (1 mg/ml) at pH 5.2;
  (iv) adalimumab (200 mg/ml), glycerol (130 mM), methionine (30 mM), arginine (60 mM, 100 mM, or 150 mM), sodium acetate (8 mM), and polysorbate 20 (1 mg/ml) at pH 5.2; or
  (v) adalimumab (240 mg/ml), glycerol (130 mM), methionine (30 mM), arginine (60 mM, 100 mM, or 150 mM), sodium acetate (8 mM), and polysorbate 20 (1 mg/ml) at pH 5.2; and (b) adalimumab (50 mg/ml, 100 mg/ml, 160 mg/ml, 200 mg/ml, or 240 mg/ml), 1,2-propanediol (130 mM), methionine (30 mM), arginine (60 mM, 100 mM, or 150 mM), sodium acetate (8 mM), and polysorbate 20 (1 mg/ml) at pH 5.2; e.g.
  (i) adalimumab (50 mg/ml), 1,2-propanediol (130 mM), methionine (30 mM), arginine (60 mM, 100 mM, or 150 mM), sodium acetate (8 mM), and polysorbate 20 (1 mg/ml) at pH 5.2;
  (ii) adalimumab (100 mg/ml), 1,2-propanediol (130 mM), methionine (30 mM), arginine (60 mM, 100 mM, or 150 mM), sodium acetate (8 mM), and polysorbate 20 (1 mg/ml) at pH 5.2;
  (iii) adalimumab (160 mg/ml), 1,2-propanediol (130 mM), methionine (30 mM), arginine (60 mM, 100 mM, or 150 mM), sodium acetate (8 mM), and polysorbate 20 (1 mg/ml) at pH 5.2; or (iv) adalimumab (200 mg/ml), 1,2-propanediol (130 mM), methionine (30 mM), arginine (60 mM, 100 mM, or 150 mM), sodium acetate (8 mM), and polysorbate 20 (1 mg/ml) at pH 5.2.

Stability of the five sets of Formulations (5X (F1-F8)) are tested at 40° C., 25° C. and 2-8° C. by visual assessment, size-exclusion chromatography (SEC) and cation-exchange chromatography (CEX) as described above.

Formation of high molecular weight species (HMWS) and low molecular weight species (LMWS) is assessed by SEC following storage for 4 and 8 weeks. Cation-exchange chromatography is used to follow % deamidated species, % oxidised species and % other related species following storage for 4 and 8 weeks. Visual score 1: clear solution, virtually free of particles; visual score 2: ~5 very small particles; visual score 3: ~10-20 very small particles; visual score 4: 20-50 particles, including larger particles; visual score 5: >50 particles, including larger particles.

Throughout the specification and the claims which follow, unless the context requires otherwise, the word 'comprise', and variations such as 'comprises' and 'comprising', will be understood to imply the inclusion of a stated integer, step, group of integers or group of steps but not to the exclusion of any other integer, step, group of integers or group of steps.

While this invention has been particularly shown and described with references to preferred embodiments thereof, it will be understood by those skilled in the art that various changes in form and details may be made therein without departing from the scope of the invention encompassed by the appended claims. It should also be understood that the embodiments described herein are not mutually exclusive and that features from the various embodiments may be combined in whole or in part in accordance with the invention.

All publications, patents, patent applications, internet sites, and accession numbers/database sequences (including both polynucleotide and polypeptide sequences) cited are herein incorporated by reference in their entirety for all purposes to the same extent as if each individual publication, patent, patent application, internet site, or accession number/database sequence were specifically and individually indicated to be so incorporated by reference.

The invention claimed is:

1. An aqueous solution comprising
   (i) a monoclonal antibody; and
   (ii) a stabilizing amount of arginine, methionine, and a C3 polyol;
   wherein the concentration of methionine is 2-50 mM and the ratio of arginine to methionine (mM/mM) is 1:1-10:1.

2. The aqueous solution of claim 1, wherein the C3 polyol is 1,2-propanediol, glycerol, or a mixture of 1,2-propanediol and glycerol.

3. The aqueous solution of claim 1, wherein the C3 polyol is present at a concentration of about 100 mM to about 500 mM.

4. The aqueous solution of claim 1, wherein the monoclonal antibody is a therapeutic antibody.

5. The aqueous solution of claim 1, wherein the monoclonal antibody is trastuzumab.

6. The aqueous solution of claim 1, wherein the monoclonal antibody is bevacizumab.

7. The aqueous solution of claim 1, wherein the monoclonal antibody is selected from trastuzumab, rituximab, bevacizumab, cetuximab and ipilimumab.

8. The aqueous solution of claim 1, wherein the monoclonal antibody is rituximab, bevacizumab, or adalimumab.

9. The aqueous solution of claim 1, wherein the monoclonal antibody is rituximab.

10. The aqueous solution of claim 1, wherein the monoclonal antibody is adalimumab.

11. The aqueous solution of claim 1, wherein the monoclonal antibody is cetuximab.

12. The aqueous solution of claim 1, wherein the monoclonal antibody is present at a concentration of about 1 mg/mL to about 300 mg/mL.

13. The aqueous solution of claim 1, wherein the arginine is present at a concentration of about 5 mM to about 100 mM.

14. The aqueous solution of claim 1, wherein the pH of the solution is between about pH 5.0 and about pH 7.0.

15. The aqueous solution of claim 1, further comprising a buffer.

16. The aqueous solution of claim 1, further comprising a non-ionic surfactant.

17. The aqueous solution of claim 1, further comprising an uncharged tonicity modifier.

18. The aqueous solution of claim 1, further comprising a charged tonicity modifier.

19. The aqueous solution of claim 1, wherein the aqueous solution is isotonic.

20. The aqueous solution of claim 1, further comprising a preservative.

21. The aqueous solution of claim 1, which is formulated for administration by subcutaneous or intramuscular injection or by intravenous injection or infusion.

22. The aqueous solution of claim 1, wherein the C3 polyol is present at a concentration of about 150 mM to about 400 mM.

23. The aqueous solution of claim 1, wherein the C3 polyol is 1,2-propanediol.

24. The aqueous solution of claim 1, wherein the C3 polyol is glycerol.

25. The aqueous solution of claim 1, wherein the C3 polyol is a mixture of 1,2-propanediol and glycerol.

26. The aqueous solution of claim 1, wherein the monoclonal antibody is a murine antibody, a chimeric antibody, a humanized antibody or a human antibody.

27. The aqueous solution of claim 1, wherein the monoclonal antibody is present at a concentration of about 10 mg/mL to about 200 mg/mL.

28. The aqueous solution of claim 1, wherein the monoclonal antibody is present at a concentration of about 50 mg/mL to about 200 mg/mL.

29. The aqueous solution of claim 27, wherein the monoclonal antibody is rituximab, bevacizumab, or adalimumab.

30. The aqueous solution of claim 1, wherein the arginine is present at a concentration of about 50 mM to about 100 mM.

31. The aqueous solution of claim 1, wherein the methionine is present at a concentration of about 2 mM to about 30 mM.

32. The aqueous solution of claim 1, wherein the pH of the solution is between about pH 5.0 and about pH 7.0.

33. The aqueous solution of claim 15, wherein the buffer is selected from the group consisting of histidine, succinate, maleate, acetate, phosphate and TRIS.

34. The aqueous solution of claim 15, wherein the buffer is present at a-concentration of about 1 mM to about 20 mM.

35. The aqueous solution of claim 15, wherein the buffer is present at a-concentration of about 2 mM to about 5 mM.

36. The aqueous solution of claim 16, wherein the nonionic surfactant is an alkyl glycoside, a polysorbate surfactant, a block copolymer of polyethylene glycol and polypropylene glycol or an alkylphenyl ether of polyethylene glycol.

37. The aqueous solution of claim 16, wherein the nonionic surfactant is dodecyl maltoside, polysorbate 80 polysorbate 20, an alkyl ether of polyethylene glycol, poloxamer 188, poloxamer 407, poloxamer 171, poloxamer 185, or 4-(1,1,3,3-tetramethylbutyl) phenyl-polyethylene glycol.

38. The aqueous solution of claim 16, wherein the nonionic surfactant is dodecyl maltoside, polysorbate 80 polysorbate 20 or poloxamer 188.

39. The aqueous solution of claim 16, wherein the nonionic surfactant is present at a concentration of about 10 µg/mL to about 2000 µg/mL.

40. The aqueous solution of claim 17, wherein the uncharged tonicity modifier is sucrose, trehalose, mannitol, sorbitol, PEG300 or PEG400.

41. The aqueous solution of claim 17, wherein the uncharged tonicity modifier is present at a concentration of about 100 mM to about 500 mM, or about 300 mM.

42. The aqueous solution of claim 18, wherein the charged tonicity modifier is sodium chloride, sodium sulphate, sodium acetate, sodium lactate, glycine or histidine.

43. The aqueous solution of claim 18, wherein the charged tonicity modifier is present at a concentration of about 25 mM to about 500 mM.

44. The aqueous solution of claim 20, wherein the preservative is phenol, m-cresol, chlorocresol, benzyl alcohol, propylparaben, methylparaben, benzalkonium chloride or benzethonium chloride.

45. The aqueous solution of claim 20, wherein the preservative is present at a concentration of about 0.01 mM to about 100 mM.

46. The aqueous solution of claim 1, wherein the arginine is present at a concentration of about 20 mM to about 100 mM.

47. The aqueous solution of claim 1, wherein the ratio of arginine to methionine (mM/mM) is 2:1-10:1.

* * * * *